US010556106B2

(12) United States Patent
Imran et al.

(10) Patent No.: US 10,556,106 B2
(45) Date of Patent: Feb. 11, 2020

(54) SYSTEM AND METHOD FOR BIPHASIC TRANSDERMAL IONTOPHORETIC DELIVERY OF THERAPEUTIC AGENTS FOR THE CONTROL OF ADDICTIVE CRAVINGS

(71) Applicant: InCube Labs, LLC, San Jose, CA (US)

(72) Inventors: Mir A. Imran, Los Altos Hills, CA (US); Talat Imran, Los Altos Hills, CA (US); Mir Hashim, Fremont, CA (US)

(73) Assignee: INCUBE LABS, LLC, San Jose, CA (US)

( * ) Notice: Subject to any disclaimer, the term of this patent is extended or adjusted under 35 U.S.C. 154(b) by 310 days.

(21) Appl. No.: 15/709,063

(22) Filed: Sep. 19, 2017

(65) Prior Publication Data

US 2018/0001084 A1    Jan. 4, 2018

Related U.S. Application Data

(60) Division of application No. 14/659,240, filed on Mar. 16, 2015, now Pat. No. 9,775,994, which is a
(Continued)

(51) Int. Cl.
*A61N 1/30* (2006.01)
*A61K 9/00* (2006.01)
(Continued)

(52) U.S. Cl.
CPC .............. *A61N 1/30* (2013.01); *A61K 9/0009* (2013.01); *A61K 9/0014* (2013.01);
(Continued)

(58) Field of Classification Search
CPC .. A61K 9/0009; A61N 1/0432; A61N 1/0448; A61N 1/30; A61N 1/325; A61N 1/303
(Continued)

(56) References Cited

U.S. PATENT DOCUMENTS 3,491,187 A    1/1970  Ely
4,325,367 A    4/1982  Tapper
(Continued)

FOREIGN PATENT DOCUMENTS

CN    1606461 A    4/2005
CN    101036825 A   9/2007
(Continued)

OTHER PUBLICATIONS

International Preliminary Report on Patentability dated Aug. 25, 2011 in PCT/US2010/023112.
(Continued)

*Primary Examiner* — Deanna K Hall
(74) *Attorney, Agent, or Firm* — Mahamedi IP Law LLP; Joel Harris

(57) ABSTRACT

Embodiments of the invention provide methods for the transdermal delivery of therapeutic agents for the treatment of addictive cravings e.g., nicotine compounds for the treatment of nicotine cravings from tobacco use. An embodiment of a method for such delivery comprises positioning at least one electrode assembly in electrical communication with a patient's skin. The assembly includes a solution comprising a therapeutic agent which passively diffuses into the skin. A dose of agent is delivered from the assembly into the skin during a first period using a first current having a characteristic e.g., polarity and magnitude, to repel the agent out of the assembly. During a second period, a second current having a characteristic to attract the agent is used to retain the agent in the assembly such that delivery of agent into skin is minimized. A dose of agent may be delivered on demand by an input from the patient.

22 Claims, 18 Drawing Sheets

Related U.S. Application Data continuation of application No. 13/466,116, filed on May 7, 2012, now Pat. No. 9,008,765, which is a continuation-in-part of application No. 12/537,243, filed on Aug. 6, 2009, now Pat. No. 8,190,252, said application No. 13/466,116 is a continuation-in-part of application No. 13/430,662, filed on Mar. 26, 2012, now Pat. No. 9,095,503.

(60) Provisional application No. 61/465,896, filed on Mar. 24, 2011, provisional application No. 61/518,486, filed on May 6, 2011, provisional application No. 61/152,251, filed on Feb. 12, 2009.

(51) Int. Cl.
*A61N 1/04* (2006.01)
*A61N 1/32* (2006.01)
*A61K 31/465* (2006.01)

(52) U.S. Cl.
CPC .......... *A61K 31/465* (2013.01); *A61N 1/0432* (2013.01); *A61N 1/0448* (2013.01); *A61N 1/303* (2013.01); *A61N 1/325* (2013.01)

(58) Field of Classification Search
USPC ............................................................. 604/20
See application file for complete search history.

(56) References Cited

U.S. PATENT DOCUMENTS

| | | | |
|---|---|---|---|
| 4,731,049 A | 3/1988 | Parsi | |
| 4,734,090 A | 3/1988 | Sibalis | |
| 4,745,925 A | 5/1988 | Dietz | |
| 4,764,164 A | 8/1988 | Sasaki | |
| 4,886,489 A | 12/1989 | Jacobsen et al. | |
| 5,052,400 A | 10/1991 | Dietz | |
| 5,207,752 A | 5/1993 | Sorenson et al. | |
| 5,310,404 A | 5/1994 | Gyory et al. | |
| 5,322,502 A | 6/1994 | Theeuwes et al. | |
| 5,328,453 A | 7/1994 | Sibalis | |
| 5,331,979 A | 7/1994 | Henley | |
| 5,385,543 A | 1/1995 | Haak et al. | |
| 5,503,632 A | 4/1996 | Haak | |
| 5,605,536 A | 2/1997 | Sibalis | |
| 5,634,899 A | 6/1997 | Shapland et al. | |
| 5,693,024 A | 12/1997 | Flower | |
| 5,797,867 A | 8/1998 | Guerrera et al. | |
| 5,830,175 A | 11/1998 | Flower | |
| 5,928,185 A | 7/1999 | Muller et al. | |
| 5,983,130 A | 11/1999 | Phipps et al. | |
| 6,018,679 A | 1/2000 | Dinh et al. | |
| 6,018,680 A | 1/2000 | Flower | |
| 6,019,877 A | 2/2000 | Dupelle et al. | |
| 6,064,908 A | 5/2000 | Muller et al. | |
| 6,115,477 A | 9/2000 | Filo | |
| 6,223,076 B1 | 4/2001 | Tapper | |
| 6,330,471 B1 | 12/2001 | Higo et al. | |
| 6,512,950 B2 | 1/2003 | Li et al. | |
| 6,553,255 B1 | 4/2003 | Miller et al. | |
| 6,689,275 B1 | 2/2004 | Gupta | |
| 6,726,920 B1 | 4/2004 | Theeuwes et al. | |
| 6,731,965 B2 | 5/2004 | Menon et al. | |
| 6,779,468 B1 | 8/2004 | Gupta | |
| 7,137,975 B2 | 11/2006 | Miller et al. | |
| 7,340,297 B2 | 3/2008 | Tamarkin et al. | |
| 7,375,139 B2 | 5/2008 | Aldred | |
| 7,437,189 B2 | 10/2008 | Matsumura et al. | |
| 7,496,401 B2 | 2/2009 | Bernabel | |
| 7,522,954 B2 | 4/2009 | Tedoldi | |
| 7,548,778 B2 | 6/2009 | Roy | |
| 7,558,625 B2 | 7/2009 | Levin et al. | |
| 7,590,444 B2 | 9/2009 | Tanioka | |
| 7,593,770 B2 | 9/2009 | Lerner | |
| 7,611,481 B2 | 11/2009 | Cleary et al. | |
| 7,816,404 B2 | 10/2010 | McCall, Jr. | |
| 8,190,252 B2 | 5/2012 | Imran | |
| 8,348,922 B2 | 1/2013 | Imran | |
| 8,417,330 B2 | 4/2013 | Imran | |
| 8,423,131 B2 | 4/2013 | Imran | |
| 8,744,569 B2 | 6/2014 | Imran | |
| 8,903,485 B2 | 12/2014 | Imran | |
| 8,961,492 B2 | 2/2015 | Imran et al. | |
| 9,008,765 B2 | 4/2015 | Imran | |
| 9,533,142 B2 | 1/2017 | Imran | |
| 2003/0018296 A1 | 1/2003 | Riddle | |
| 2003/0060798 A1 | 3/2003 | Fischer et al. | |
| 2003/0199808 A1 | 10/2003 | Henley et al. | |
| 2004/0138646 A1 | 7/2004 | Walla | |
| 2005/0020487 A1 | 1/2005 | Klaus et al. | |
| 2005/0085751 A1 | 4/2005 | Daskal et al. | |
| 2005/0137626 A1 | 6/2005 | Pastore | |
| 2005/0165393 A1 | 7/2005 | Eppstein | |
| 2005/0209565 A1 | 9/2005 | Yuzhakov | |
| 2005/0213286 A1 | 9/2005 | Michel et al. | |
| 2005/0238704 A1 | 10/2005 | Zumbrunn et al. | |
| 2005/0273046 A1 | 12/2005 | Kwiatkowski et al. | |
| 2006/0025715 A1 | 2/2006 | Henley et al. | |
| 2006/0216339 A1 | 9/2006 | Ambron et al. | |
| 2006/0229549 A1 | 10/2006 | Hause et al. | |
| 2006/0258973 A1 | 11/2006 | Volt | |
| 2007/0065521 A1 | 3/2007 | Venkataraman et al. | |
| 2007/0066934 A1 | 3/2007 | Etheredge et al. | |
| 2007/0083185 A1 | 4/2007 | Carter | |
| 2007/0083186 A1 | 4/2007 | Carter et al. | |
| 2007/0224253 A1 | 9/2007 | Franklin | |
| 2008/0027369 A1 | 1/2008 | Carter et al. | |
| 2008/0058699 A1 | 3/2008 | Hause et al. | |
| 2008/0058700 A1 | 4/2008 | Hause et al. | |
| 2008/0081051 A1 | 4/2008 | Sabin et al. | |
| 2008/0114282 A1 | 5/2008 | Carter | |
| 2008/0154178 A1 | 6/2008 | Carter et al. | |
| 2008/0287497 A1 | 11/2008 | Anderson et al. | |
| 2009/0036821 A1 | 2/2009 | Lai | |
| 2009/0062720 A1 | 3/2009 | Anderson et al. | |
| 2009/0124572 A1 | 5/2009 | Nelson | |
| 2009/0130189 A1 | 5/2009 | Nicklasson | |
| 2009/0163597 A1 | 6/2009 | Goto et al. | |
| 2009/0171313 A1 | 7/2009 | Yamamoto et al. | |
| 2009/0221985 A1 | 9/2009 | Bukshpan et al. | |
| 2009/0254018 A1 | 10/2009 | Nakayama | |
| 2009/0259176 A1 | 10/2009 | Yairi | |
| 2009/0264855 A1 | 10/2009 | Phipps et al. | |
| 2009/0281475 A1 | 11/2009 | Nisato et al. | |
| 2009/0299264 A1 | 12/2009 | Matsumura et al. | |
| 2009/0299267 A1 | 12/2009 | Durand | |
| 2010/0204637 A1 | 8/2010 | Imran | |
| 2010/0232464 A1 | 9/2010 | Taniguchi et al. | |
| 2010/0331759 A1 | 12/2010 | Imran | |
| 2010/0331810 A1 | 12/2010 | Imran | |
| 2010/0331811 A1 | 12/2010 | Imran | |
| 2011/0009805 A1 | 1/2011 | Imran | |
| 2011/0082411 A1 | 4/2011 | Imran | |
| 2012/0232464 A1 | 9/2012 | Imran | |
| 2013/0023815 A1 | 1/2013 | Imran | |
| 2013/0023850 A1 | 1/2013 | Imran | |

FOREIGN PATENT DOCUMENTS

| | | |
|---|---|---|
| EP | 0090425 A1 | 10/1983 |
| JP | 1985-156475 | 7/1985 |
| JP | 1991-045272 | 2/1991 |
| JP | 1995-222806 | 8/1995 |
| JP | 2004-508148 | 3/2004 |
| JP | 2006-0345931 | 12/2006 |
| JP | 2007-521258 | 8/2007 |
| JP | 2007-237002 | 9/2007 |
| JP | 2009-039557 | 2/2009 |
| JP | 2012-517321 | 2/2010 |
| WO | WO 1996/010442 | 4/1996 |

(56) References Cited

FOREIGN PATENT DOCUMENTS

| WO | WO 2002/022204 | 3/2002 |
|---|---|---|
| WO | WO 2011/044175 A2 | 4/2011 |

OTHER PUBLICATIONS

International Preliminary Report on Patentability dated Aug. 25, 2011 in PCT/US2010/023744.
International Search Report and Written Report and Notice of Transmittal of same dated Feb. 25, 2011 in PCT/US2010/040109.
International Search Report and Written Opinion and Notice of Transmittal of same dated Jun. 24, 2011 in PCT/US2010/051541.
International Search Report and Written Opinion and Notice of Transmittal of Same dated Sep. 27, 2010 in PCT/US2010/023744.
International Search Report and Written Opinion and Notice of Transmittal of Same dated Sep. 27, 2010 in PCT/US2010/023112.
Murthy et al. "Irontophoresis: Transdermal Delivery of Iron Iontophoresis," J. Pharm. Sci., 98(8): 2670-2676 (Aug. 2009).
Examination Report dated Aug. 13, 2013 in Australian Application No. 2010213975.
McLaughlin, G.W., et al., "Biphasic Transdermal Iontophoretic Drug Delivery Platform," Conf. Proc. IEEE Eng. Med. Biol.Soc. Aug. 2011: 2011:1225-8.
International Search Report and Written Opinion dated Oct. 31, 2012 as issued in PCT/US2012030633.
International Preliminary Report on Patentability dated Jan. 12, 2012 in PCT/US2010/040109.
International Preliminary Report on Patentability dated Apr. 19, 2012 as issued in PCT/US2010/051541.
Office Action dated Feb. 4, 2014 in Japanese Application No. 2011-550168.
European Search Report dated Jan. 31, 2014 in Application No. 10741574.7.
Office Action dated Jul. 1, 2014 in Japanese Application No. 2011-550168.
European Extended Search Report dated Oct. 10, 2014 in EP Application 12760602.8.
Second Office Action dated Aug. 31, 2015 in Chinese Application No. 201280023328.4.
International Preliminary Examination Report dated Aug. 23, 2012 issued in PCT/US2011/024259.
International Search Report and Written Opinion dated Oct. 28, 2011 issued in PCT/US2011/024259.
First Office Action dated Jul. 19, 2013 in Chinese Application No. 2010800133287.
Examination Report dated Jul. 1, 2016 in Australian Application No. 2012230701.
Office Action dated Feb. 13, 2018 in Japanese Application No. 2016-234997.
Office Action dated Feb. 21, 2018 in Japanese Application No. 2017-083298.

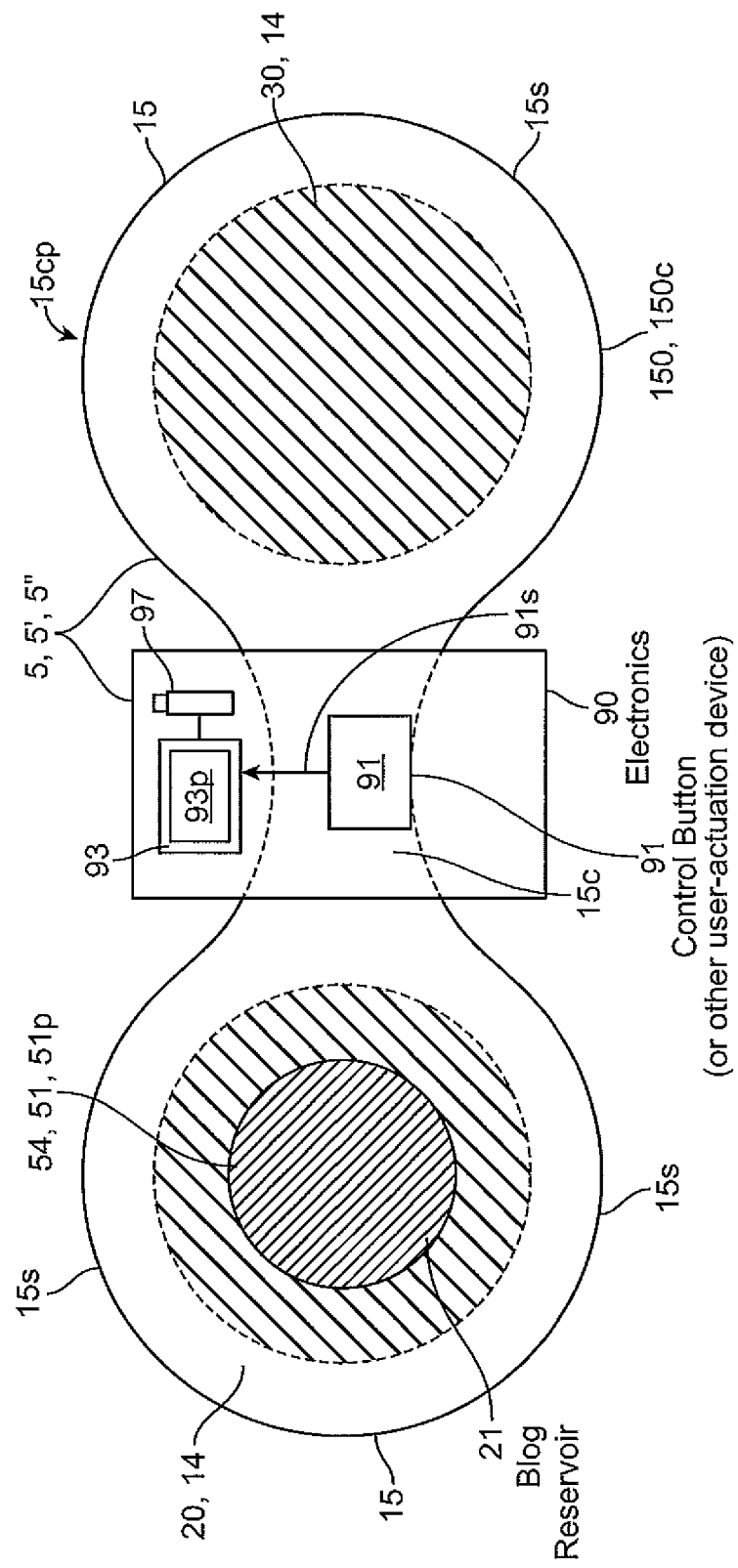

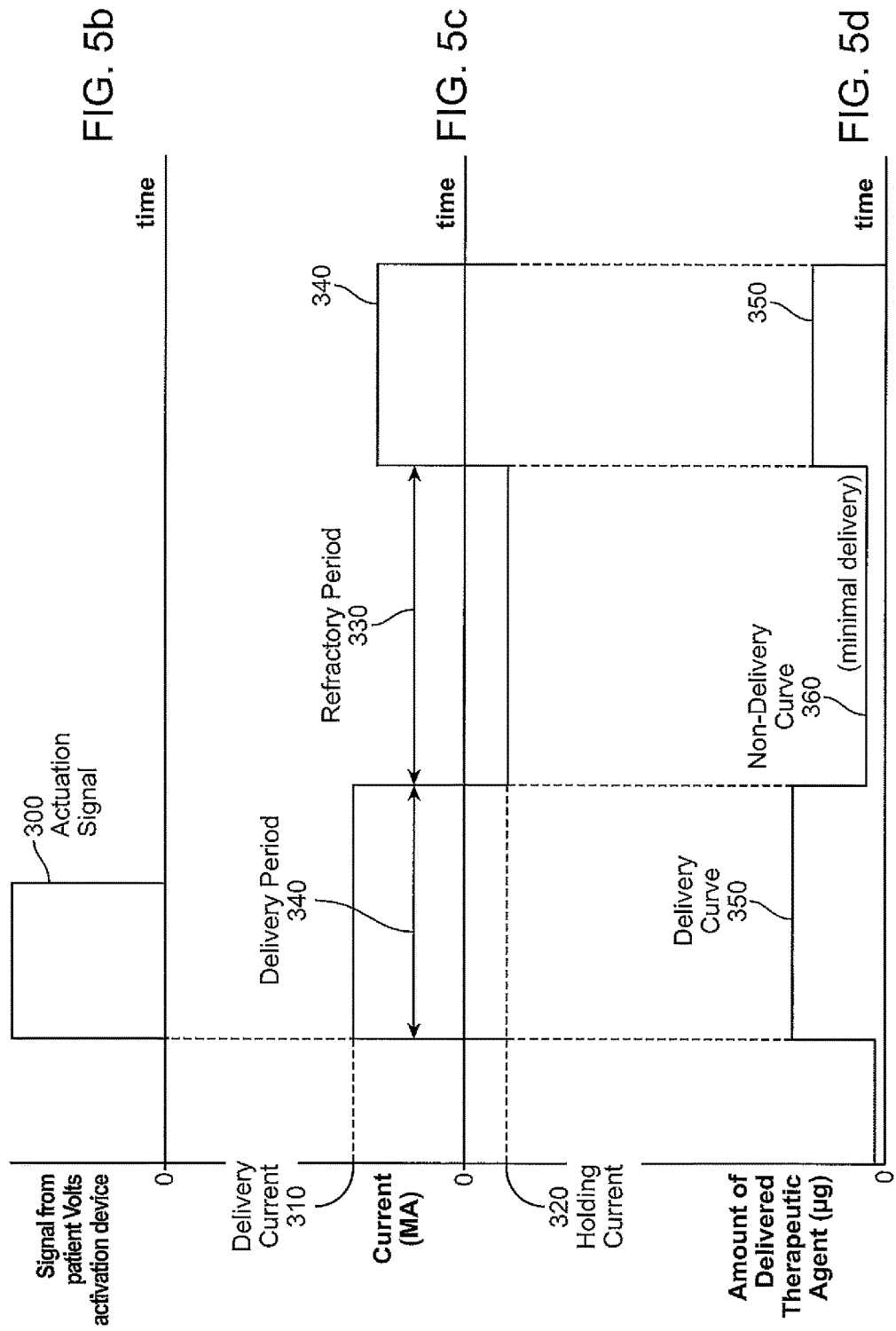

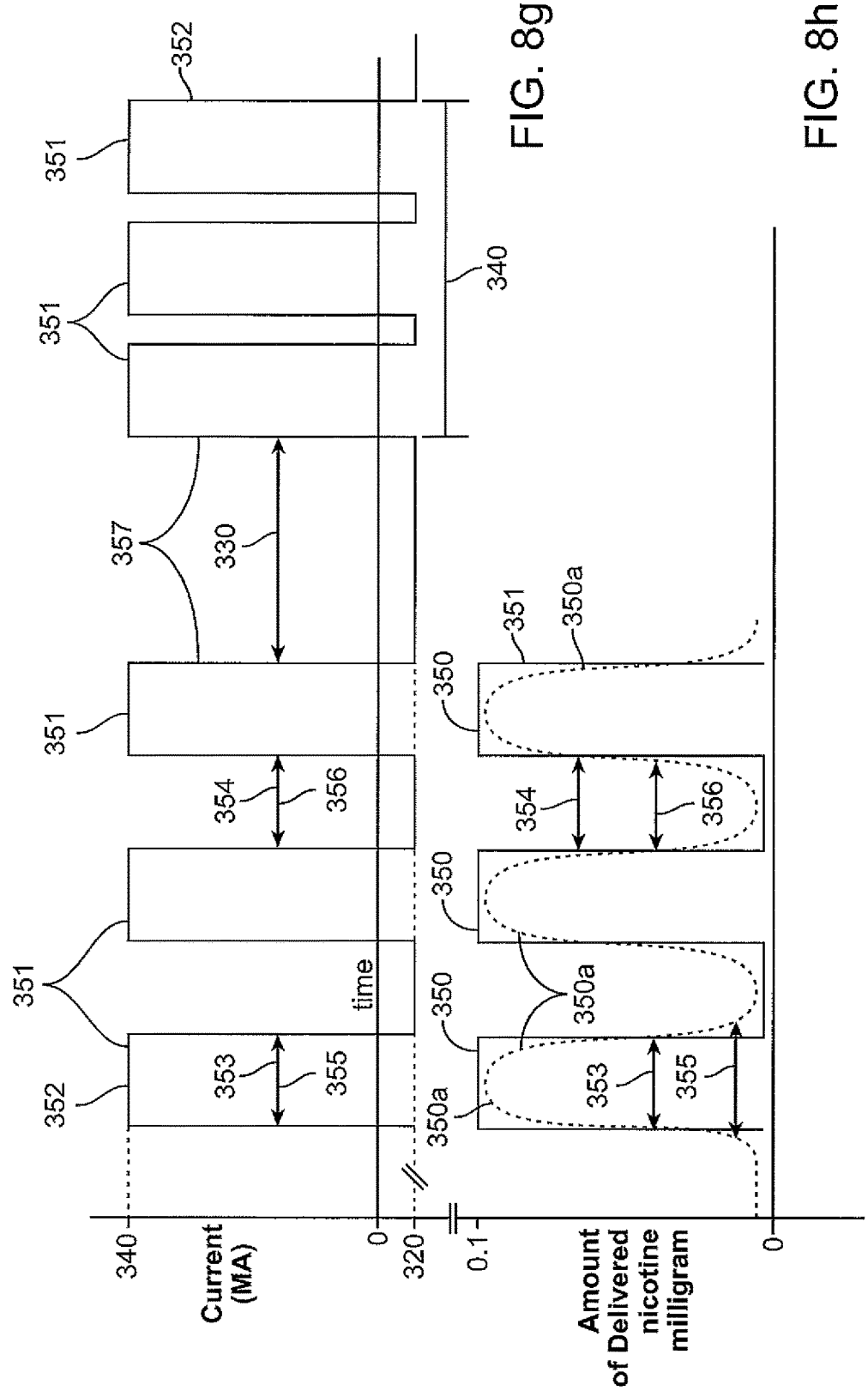

SYSTEM AND METHOD FOR BIPHASIC TRANSDERMAL IONTOPHORETIC DELIVERY OF THERAPEUTIC AGENTS FOR THE CONTROL OF ADDICTIVE CRAVINGS

RELATED APPLICATIONS

This application is a divisional of U.S. patent application Ser. No. 14/659,240 filed Mar. 16, 2015, which is a continuation of U.S. patent application Ser. No. 13/466,116, filed May 7, 2012, now U.S. Pat. No. 9,008,765, which claims the benefit of U.S. Provisional U.S. Patent Application Ser. No. 61/518,486, entitled "BIPHASIC TRANSDERMAL IONTOPHORETIC SYSTEM FOR THE TRANSDERMAL DELIVERY OF THERAPEUTIC AGENTS FOR THE CONTROL OF ADDITIVE CRAVINGS" filed May 6, 2011; which is fully incorporated by reference herein for all purposes. Said Ser. No. 13/466,116 is also a continuation-in-part of U.S. patent application Ser. No. 12/537,243, filed Aug. 6, 2009, now U.S. Pat. No. 8,190,252, which claims the benefit of U.S. Provisional U.S. Patent Application No. 61/152,251, entitled "Kit, System and Method for Transdermal Iontophoretic Delivery of Therapeutic Agents", filed Feb. 12, 2009; both of which are fully incorporated by reference herein for all purposes. Said Ser. No. 13/466,116 is also a continuation-in-part of U.S. patent application Ser. No. 13/430,662, filed Mar. 26, 2012, now U.S. Pat. No. 9,095,503, which claims the benefit of U.S. Provisional U.S. Patent Application Ser. No. 61/465,896, entitled "Biphasic Transdermal Iontophoretic System For The Transdermal Delivery Of Therapeutic Agents" filed Mar. 24, 2011; both of which are fully incorporated by reference herein for all purposes.

This application is related to U.S. patent application Ser. No. 12/898,671, filed Oct. 5, 2010, now U.S. Pat. No. 8,903,485, which claims the benefit of U.S. Provisional Patent Application Ser. No. 61/249,247 filed Oct. 6, 2009, both of which are fully incorporated by reference herein for all purposes.

FIELD OF THE INVENTION

Embodiments described herein relate to assemblies and methods for transdermal drug delivery. More specifically, embodiments described herein relate to assemblies and methods for iontophoretic transdermal delivery of drugs and other therapeutic agents. Still more specifically, embodiments described herein relate to assemblies and methods for using iontophoretic transdermal delivery of therapeutic agents to treat addictive cravings.

BACKGROUND

Cigarette and other forms of tobacco addiction affect millions of Americans. It destroys quality of life, causes many mortal diseases including heart and lung diseases and multiple forms of cancer. According to the CDC, smoking causes nearly 500,000 deaths each year in the U.S. alone due to heart and lung disease and numerous forms of cancer. Other forms of tobacco use such as cigar and pipe smoking as well as chewing tobacco are also responsible for countless deaths each year due to mouth and throat and other forms of cancer. Cigarette smoking and other forms of tobacco addiction are all due to the presence of nicotine which is a highly addictive alkaloid substance found in the tobacco plant. The addiction is due to number of psychoactive effects that nicotine has on the brain including feeling of satisfaction, calm, relaxation, etc. In case of cigarettes, matters are made worse by the fact that tobacco companies actually adjust the dose of nicotine in cigarettes to maximize addictive behavior. They do this in part by designing cigarettes to give the smoker an immediate spike of nicotine upon the first several puffs.

Many smoking cessation program involve stopping smoking altogether (i.e., going cold turkey). However, one of the most difficult aspects of this or other forms of tobacco cessation is the craving for nicotine and thus a cigarette created when the user suddenly stops smoking. There are several nicotine delivery products to address this pro problem which do not involve smoking. Two of the more popular forms used in smoking cessation programs include nicotine containing transdermal drug delivery patches nicotine containing gum. However both have a number of limitations. First, neither is able to mimic the rapid or spike dose delivery of nicotine achieved from smoking a cigarette. Consequently, the smoker doesn't get the same psychoactive effect and as a result the user can still develop cravings even when they are receiving nicotine from one or both products. Further, for these same reasons, neither may be effective for the treatment of breakthrough cravings. Breakthrough craving is a craving that comes on suddenly for short periods of time and is not easily controlled. For cigarette smokers, the characteristics of breakthrough cravings may vary from person to person depending upon their smoking habits including the number of cigarettes they were smoking each day, years of smoking and overall brain chemistry. Nether approach can treat such cravings since they deliver fixed amounts of nicotine over an extended period of time and cannot be adjusted for a given user. Both methods are susceptible to excessive self-administration from the user applying multiple patches and/or chewing multiple lozenges. The user is also susceptible to varying delivery in the case of transdermal patches since manufactures make one size fits all transdermal fixed dose nicotine patches which don't account for differences between users. Further, transdermal patches also suffer from the limitation of over-delivery since the user continues to receive nicotine via passive diffusion from the patch even after their craving has been satisfied. This can result in the user habituating to even higher doses of nicotine. Thus, there is a need for improved methods of nicotine delivery for the treatment of cigarette/nicotine cravings occurring with smoking cessation plans. The same need also applies to other forms of tobacco use including cigar, pipe and chewing tobacco which result in nicotine addiction, Transdermal iontophoresis is a non-invasive method of propelling high concentrations of a drug or other therapeutic agent through the skin of a human or other animal by repulsive electromotive force using a small electrical charge. The electrical charge repels ionized (i.e., charged) forms of the drug or other therapeutic agent. Using such an approach, doses of pain medication can be delivered to the patient using a skin contacting patch containing pain medication that has been dissolved in a solution disposed within the patch. The application of a current causes the dissolved medication to be propelled from the solution through a contacting layer of the patient and into the skin. However, over-administration/overdose remains a problem for such devices due to the fact that the pain medication continues to passively diffuse from the patch reservoir into the patient even when the iontophoretic current is off due to concentration gradients between the patch and the skin (under the principles of Fickian diffusion). Also, there is nothing to stop the patient from overdosing themselves by reactivating the device or even leaving the current on continuously to give themselves repetitive or even continuous doses. Improved systems and methods are needed for preventing over-administration of drugs due to passive diffusion as well as excessive administration by the patient.

BRIEF SUMMARY

Embodiments of the invention provide methods and assemblies for the transdermal delivery of drugs and other therapeutic agents to humans, mammals and other animals. Many embodiments provide a biphasic transdermal iontophoretic system having a delivery current to deliver doses of a therapeutic agent over a delivery period and a holding current to substantially halt or reduce the delivery of agent during a non-delivery period. Such embodiments can be configured to allow for repetitive cycles of delivery and non-delivery of drugs and other therapeutic agents to treat various conditions including for example, addictive cravings. Further, various embodiments provide systems and methods allowing for on-demand initiation of a delivery period (e.g., by the patient, caregiver or other person) to allow for treatment of various acute conditions such as craving control, pain, nausea (e.g., chemotherapy induced), migraine headache and other conditions. In particular embodiments such systems and methods can be configured for use in the delivery of various nicotine compounds (e.g., nicotine salts) for treatment of a patient's cigarette/nicotine cravings occurring smoking cessation or reduction. Cigarette/nicotine craving refers to the patient's craving for a cigarette and/or nicotine from a cigarette which may occur as a result of the patient ceasing or reducing his or her use of cigarettes. Such embodiments can also be adapted for treatment of cravings resulting from other forms of tobacco addictions such as those cravings occurring from other forms of inhaled tobacco use such as pipe, cigar or electronic cigarette use as well as use of chewing tobacco. In other particular embodiments, such systems and methods can be adapted for delivery of other compounds used for the treatment of other chemical based addictions such as methadone (including its analogues and derivatives) or other synthetic opiode for the treatment of heroin or other opiode-based addiction as well as various compounds for the treatment of cocaine addiction.

Still other embodiments of systems and methods of the invention provide for controlled initiation of a delivery period and/or cycles of delivery and non-delivery by a controller such as a microprocessor or other controller known in the art (e.g., an analogue controller). Such embodiments can be configured for the cyclical delivery of a variety of therapeutic agents including, for example, various nicotine compounds (e.g., nicotine analogues and their salts) for the treatment of nicotine cravings resulting from cessation/reduction of various forms of tobacco use, e.g., cigarette smoking. Further, such embodiments are particularly useful for the delivery of therapeutic agents where the time course of delivery of the agent needs to be controlled to produce a desired therapeutic effect, and/or to minimize adverse effects to the patient (e.g., re-habituation to higher levels of nicotine due to over delivery) Such controlled initiation (either of a delivery period or cycle of delivery and non-delivery periods) can be incorporated into a delivery regimen which can be programmed into the controller either directly, wirelessly or by means of a memory device operably coupled to the controller. The system can be configured to allow the program to be selected by a doctor, pharmacist, or other medical care provider. The selection can be done directly by the medical care provider via an input device (e.g., a touch screen) coupled to the controller or wirelessly using a wireless device such as a cell phone, tablet device or like device. In either case, lockout codes can be employed to prevent anyone but the medical care provider from entering or changing a particular delivery regimen.

One embodiment provides a method for the transdermal iontophoretic delivery of a therapeutic agent for treatment of addictive cravings, such as a nicotine compound for the treatment of addictive cravings for cigarettes, cigars or other tobacco product occurring during cessation or reduction in the use of the tobacco product. The method comprises positioning at least one electrode assembly in electrical communication with a patient. The electrode assembly includes a skin contacting layer and a solution having a dissolved therapeutic agent (e.g., a salt of nicotine or a nicotine analogue) having an electrical charge, wherein the dissolved agent passively diffuses into the skin without the application of an external force. A first dose of agent (such as nicotine or a nicotine analogue) is delivered from the electrode assembly into the skin during a first period using a first current having a polarity and voltage to repel the agent out of the assembly. The dose may be delivered continuously or in a series of bursts, for example, to mimic or simulate the nicotine delivery profile from patient's taking puffs on cigarettes. Such bursts may have a square wave, half sign wave, trapezoid other shape. Other delivery patterns for simulation of delivery profiles from other forms of tobacco use (e.g., cigar, electronic cigarette, chewing tobacco) or other addictive substances are also contemplated. Also, the dose can be titrated to the characteristics of a particular patient, such as their weight and smoking habits (e.g., number of cigarettes smoked per day and how much they have de-habituated). During a second period, a second current having a polarity and voltage to attract the agent is used to retain the agent in the assembly such that delivery of the agent into the skin during the second period is minimized so as to reduce the likelihood of unwanted and/or over delivery of the agent. For embodiments delivering nicotine compounds to treat smoking addiction, this minimized delivery prevents the patient from experiencing the psychoactive effects associated with nicotine during this second period which can cause them habituate to higher levels of nicotine and/or slow their progress in de-habituating. The first period comprises a delivery period and the second period comprises a non-delivery period, which together, comprise a delivery cycle period. The delivery cycle period can then be repeated as needed to reduce the addictive cravings in the patient. In particular embodiments, one or more delivery parameters such as the dose delivered during a delivery period and the length of the delivery and non-delivery periods can be determined or titrated based upon one or more parameters of the patient's smoking pattern. Such parameters can include, for example, the duration of each puff, puff volume, the interval between puffs and total number of puffs. In this way, the delivery profile of nicotine compound delivered by embodiments of the invention can more closely approximate or mimic the nicotine delivery profile from the patient's actual use of cigarettes (or other form of inhaled tobacco). In use, this approach can reduce nicotine cravings since the nicotine delivered during a delivery period/cycle more closely approximates that which the patient gets from the smoking of a cigarette or other form of tobacco.

In related embodiments, the dose of the therapeutic agent during delivered during a delivery period and/or during a delivery cycle can be decreased over time to de-habituate the patient from their addiction. In specific embodiments, the dose of therapeutic agent can be re-titrated (after a first initial titration) to reflect the patient's progress in their addictive behavior cessation plan. For example, in the case of a cigarette smoking cessation plan, a delivered dose of nicotine can be re-titrated based on one or more of the number of days since the patient started the plan, the number of cigarettes they are currently smoking, the change versus when they started the smoking cessation/reduction program and the number and of severity of cravings the patient is currently experiencing and the change versus when they started the smoking cessation/reduction program.

In use, these and related embodiments provide an approach for the controlled transdermal delivery of a therapeutic agent for the treatment of addictive cravings (e.g., nicotine and opiode cravings) which provides several benefits. First, through the use of a titrated and/or burst dosing it more closely approximates the dose delivered during the addictive behavior (e.g., smoking a cigarette) producing a similar psycho-active response as the behavior thus, reducing cravings. Second, the likelihood of over delivery and/or the patient habituating to unwanted delivered doses is reduced since passive diffusion during non-delivery periods is minimized. One or both of these factors can help a patient quit an addictive behavior such as cigarette smoking faster and with greater success (e.g., reduced likelihood of relapse) over conventional approaches.

Further details of these and other embodiments and aspects of the invention are described more fully below, with reference to the attached drawing figures.

BRIEF DESCRIPTION OF THE DRAWINGS

FIG. 5a is a top down view showing an embodiment of an on demand user-activated transdermal delivery system including a patch assembly.

FIGS. 5b, 5c and 5d are time sequence graphs illustrating an embodiment of a patient controlled or other "on-demand" biphasic transdermal iontophoretic delivery system having a delivery current and a holding current so as to cycle between delivery periods and non-delivery periods of a therapeutic agent such as nicotine for the treatment of nicotine cravings from tobacco use. FIG. 5b shows an activation signal for initiating a drug delivery cycle, the signal generated by a patient activated device or other signal generation means; FIG. 5c shows an embodiment of a current waveform initiated by the activation signal the waveform having a delivery current and holding current; FIG. 5d shows an embodiment of a drug delivery profile corresponding to the periods of delivery current and holding current.

FIG. 6a shows a top view, FIG. 6b shows a bottom view.

FIG. 8g illustrates an embodiment of a burst mode delivery profile/curve for burst mode delivery of a nicotine compound. FIG. 8h illustrates the resulting nicotine delivery curve and comparison to the delivery curve for smoking a cigarette or other inhaled form of tobacco.

FIG. 10a shows the cumulative input vs. the estimated system response based on an optimum cross-correlation FIR filter response of the measured system response; FIG. 10b plot shows the density input vs. the estimated system response based on an optimum cross-correlation FIR filter response of the measured system response.

DETAILED DESCRIPTION OF THE INVENTION

Various embodiments described herein provide a device, system and method for the transdermal iontophoretic delivery of various therapeutic agents including therapeutic agents for the treatment of various addictions. Such addictions can include addictions to various chemical compounds, e.g., nicotine and the addictive delivery modes for that compound, e.g., cigarette smoking. Many embodiments provide devices, systems and methods for the biphasic transdermal delivery of various therapeutic agents including therapeutic agents for the treatment of various addictions and addiction related cravings. Such therapeutic agent for the treatment of addiction related cravings can include without limitation, nicotine compounds for the treatment of nicotine cravings resulting from cigarette or other tobacco addiction (e.g., cigar, pipe, chewing tobacco, etc.); methadone and other synthetic opioid for the treatment of cravings resulting from heroin addiction to heroin or other opioid; and one or more of Acetylcysteine, Baclofen, Bupropion, Vanoxerine, and Vigabatrin or other related compound for the treatment of cravings resulting from cocaine addiction.

Figure 1:
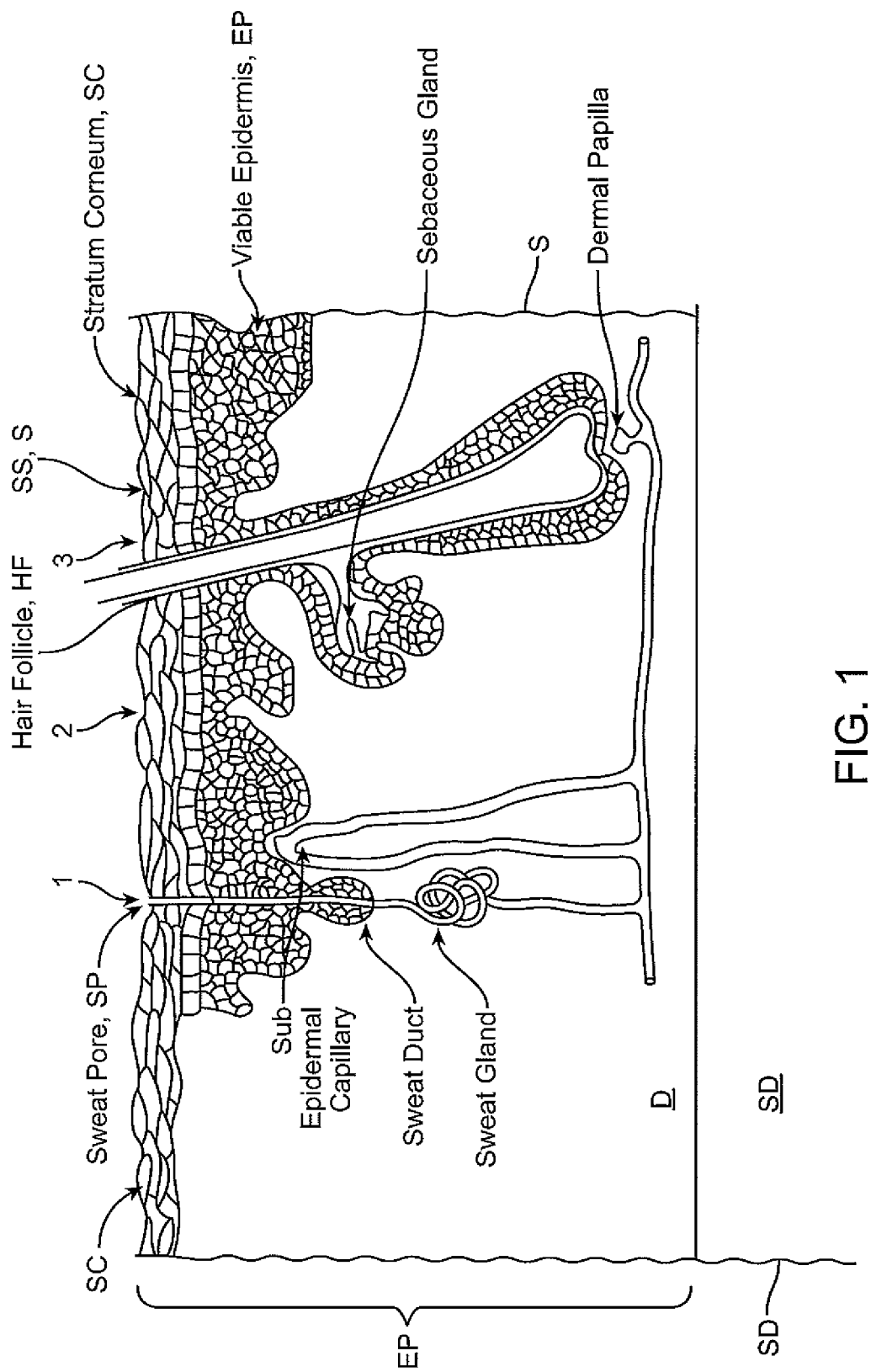
FIG. 1 is a cross sectional view showing the three main layers of the skin, the epidermis, the dermis and subcutaneous tissue as well as the passageways into the skin.

As used herein, the term transdermal delivery refers to the delivery of a compound, such as a drug or other therapeutic agent, through one or more layers of the skin (e.g., epidermis, dermis, etc.). Referring now to FIG. 1, the layers of the skin include the epidermis EP, dermis D and subdermis SD. The upper most layer of the epidermis includes the stratum corneum SC, a dead layer of skin (having a thickness of about 10 to 40 μm) and the viable epidermis EP. Transdermal delivery can proceed by one of the three passage ways into the skin, via 1, the sweat pores SP, 2, the hair follicles HF or via permeation 3 through the epidermis EP (starting at the stratum corneum) and the dermis.

Iontophoresis is a non-invasive method of propelling high concentrations of a charged substance, known as the active agent, transdermally by repulsive electromotive force using a small electrical charge. The active agent can include a drug or other therapeutic agent. The charge is applied by an electrical power source to an active electrode assembly placed on the skin which contains a similarly charged active agent and a solvent in which it is dissolved. Current flows from the electrode assembly through the skin and then returns by means of a return or counter electrode assembly also placed on the skin. A positively charged electrode assembly, termed the anode will repel a positively charged active agent, or anion, into the skin, while a negatively charged electrode assembly, termed the cathode, will repel a negatively charged active agent, known as a cation, into the skin.

Referring now to FIGS. 2-4b, an embodiment of a system 5 for the transdermal iontophoretic delivery of a therapeutic agent 51 to a tissue site TS (such as the arm A) also referred to as a delivery site TS, on the skin S of patient may comprise at least two electrode assemblies 14 including an active electrode assembly 20 and a return electrode assembly 30 and a power supply 100. Active electrode assembly 20 is used to deliver the therapeutic agent through skin S via current delivered to the skin from power supply 100. Return electrode assembly 30 provides a return path for current (e.g., current 60) to power supply 100. Collectively, the active and return electrode assemblies 20 and 30 comprise a transdermal iontophoretic delivery device 10 also described herein as patch device 10. In embodiments using an alternating current, both electrode assemblies 14 can be configured as active and return electrode assemblies 20 and 30 depending on the direction of current flow. In some cases for sake of brevity, electrode assembly 14, active electrode assembly 20 and/or return electrode assembly 30 will sometimes be referred to as electrode 14, active electrode 20 and return electrode 30 respectively.

In many embodiments, the electrode assemblies 14 (e.g., active and return assemblies 20 and 30) comprise or are otherwise disposed on one or more patches 15 configured to be applied to the skin surface. Patches 15 are conformable to a contour CR of a skin surface S and can be fabricated from layers of elastomeric or other flexible polymer material. In some embodiments, two or more electrode assemblies 14 including active and return electrode assemblies 20 and 30 can be placed on a single patch 15. In other embodiments, system 5 can include separate patches 15 for electrode assemblies 14, for example, a first patch 15' for the active electrode assembly 20 and a second patch 15" for the return electrode assembly 30. In other embodiments, three or more patches 15 can be used so as to have either multiple active electrode assemblies 20 or return electrode assemblies 30 or both. For example, in one embodiment, system 5 can comprise three patches 15; including two patches containing active electrode assemblies 20 and a third patch 15 containing a return electrode assembly 30. Other combinations of multiple patches and electrode assemblies are also contemplated, e.g., four patches, two for active electrode assemblies 20 and two for return electrode assemblies 30.

Figure 2:
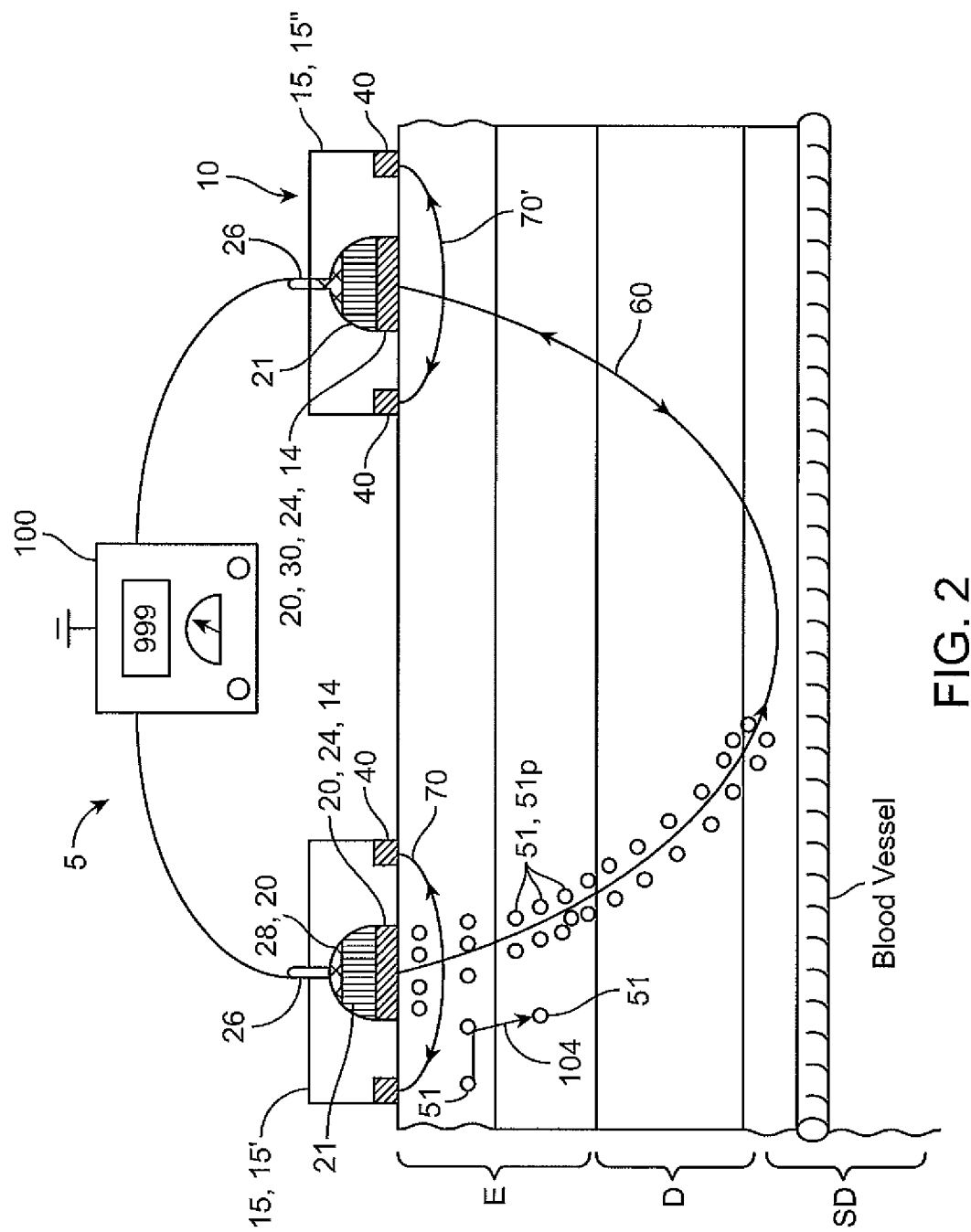
FIG. 2 is a lateral view of an embodiment of a system for the transdermal iontophoretic delivery of various therapeutic agents using delivery and lateral electrodes.

In many embodiments, active electrode assembly 20 can comprise a reservoir 21 for the therapeutic agent, a tissue contacting porous portion 24 in fluidic communication with the reservoir, an adhesive portion 25 for adhering the assembly to the skin, and an electrical connector 26 for coupling the electrode assembly 20 to an electrical power supply 100 as is shown in the embodiment of FIG. 2. Reservoir 21 can be sized for the particular dose of therapeutic agent to be delivered. In various embodiments, the power supply 100 can include various features to facilitate use by medical personnel both in a hospital setting and in the field. For example, the power supply can include or be configured to be coupled to a bar code reader (not shown) for reading bar codes positioned on one or more of electrode assemblies 14, patches 15 or power supply 100.

Tissue contacting portion 24 is also electrically conductive (herein conductive) so as to function as an active electrode 20 and/or return electrode 30. This can be achieved by fabricating tissue contacting portion 24 from conductive porous materials (e.g., conductive carbon or other conductive fibers) and/or by having it become wetted with a conductive embodiment of solution 54 (the conductivity being due to therapeutic agent 51 or various electrolytes added to the solution 54). Connector 26 can extend into or otherwise make electrical contact with tissue contacting portion 24 so to be electrically coupled to portion 24. In some embodiments, connector 26 can be coupled to a conductive element 28 positioned within the electrode assembly 14 and coupled to conductive porous portion 24. One or more of conductive element 28, conductive layer 34 (described below) as well as lateral electrodes 40 (also described below) can comprise various conductive materials including stainless steel, carbon, silver chloride (AgCl) or other conductive materials known in the art.

Figure 4A:
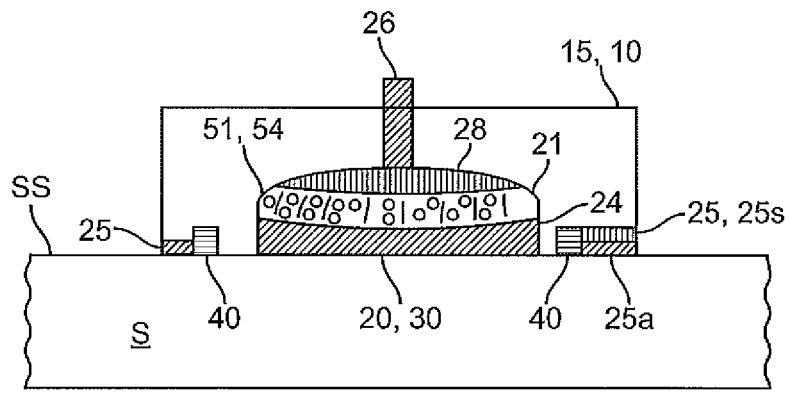
FIGS. 4a and 4b are side and top views showing an embodiment of a skin patch including an active electrode and lateral electrodes.
Figure 4B:
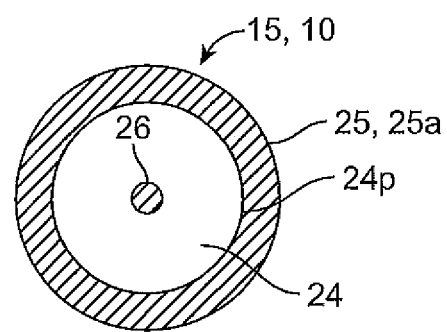

Typically, adhesive portion 25 will surround the perimeter 24p of porous portion 24 as is shown in the embodiment of FIGS. 4a and 4b, though other arrangements are also contemplated. In various embodiments, porous portion 24 can comprise a porous layer 24 that in turn comprises various porous materials including polymers foams, membranes or weaves of polymer fibers known in the art including polyesters, PETs and like materials. Adhesive portion 25 may be attached to porous layer 24 and include various releasable adhesives known in the art. The adhesive portion 25 can comprise an adhesive layer 25a, such as one or more releasable adhesives attached to a substrate layer 25s, which can comprise various hydrogels, polyurethanes, silicones or like polymeric materials. The size and configuration of adhesive portion 25 can be adapted for the particular skin location (e.g., arm vs. leg, amount of hair, etc.) and type of skin (e.g., pediatric vs. geriatric etc., amount of hair, etc.).

Figure 3A:
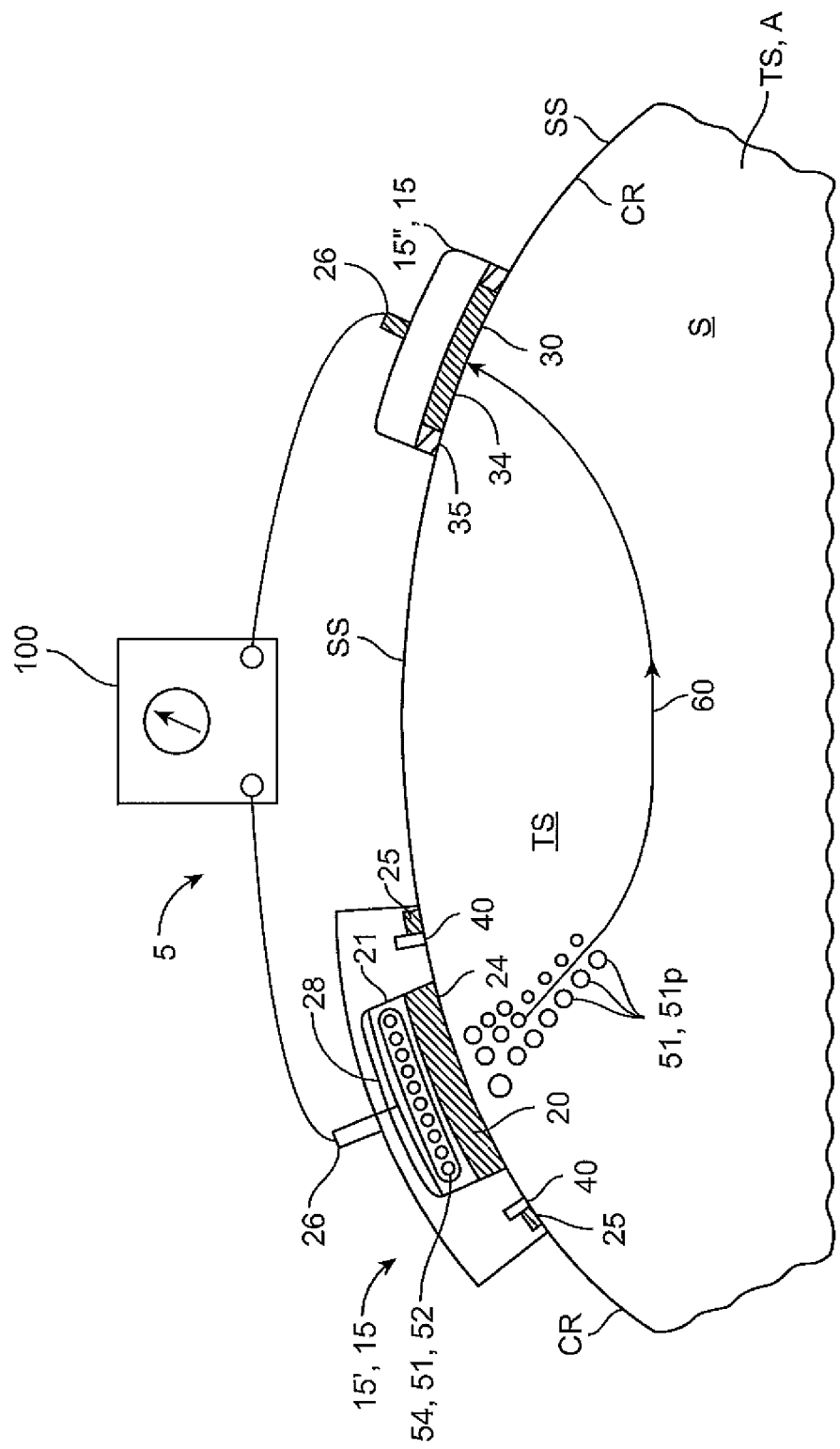
FIG. 3a is a schematic side view showing placement of an embodiment of a transdermal iontophoretic patch device on the surface of the skin, wherein the device comprises an active electrode assembly and a return electrode assembly.
Figure 3B:
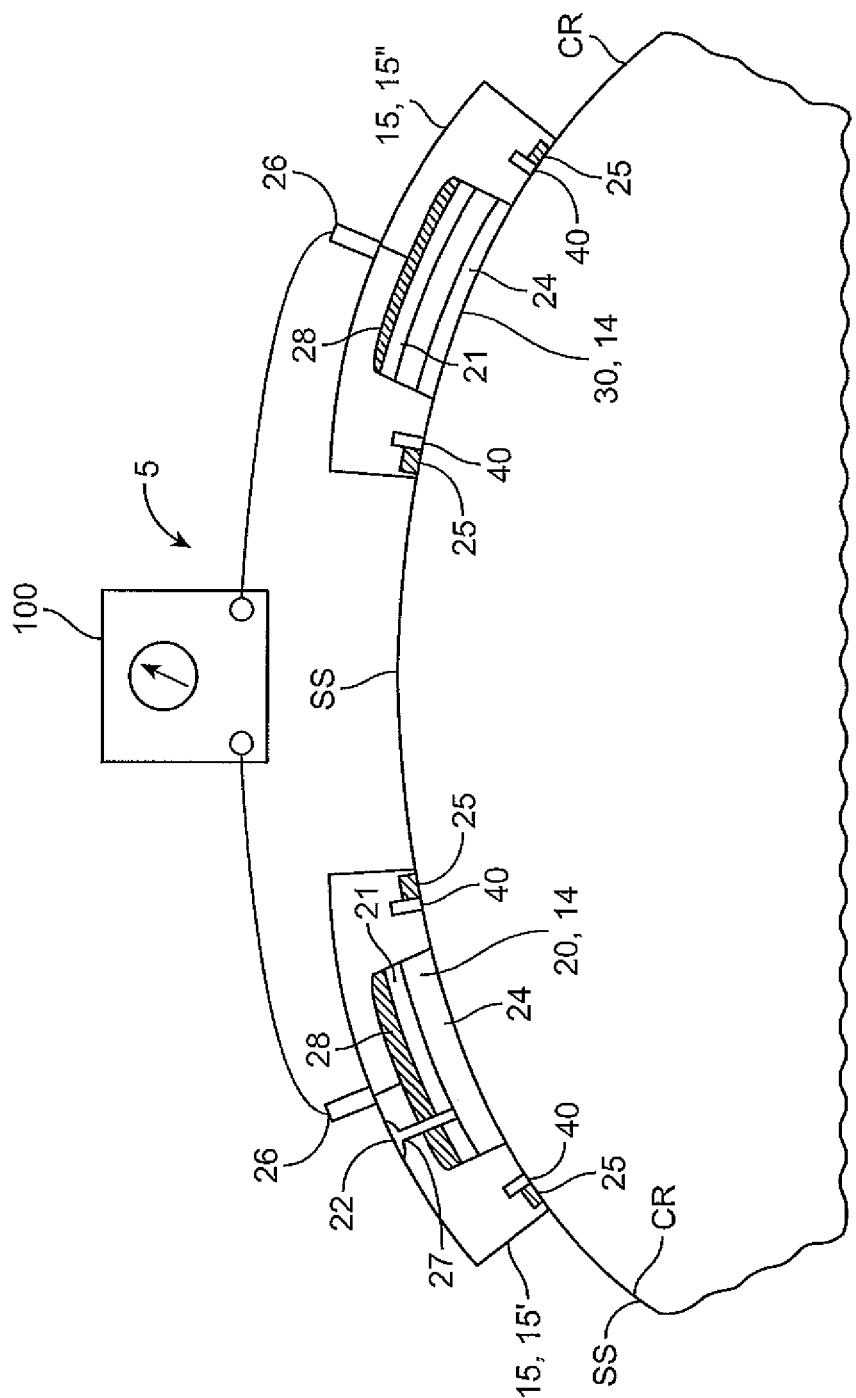
FIG. 3b is a schematic side view showing placement of an embodiment of transdermal iontophoretic patch device on the surface of the skin, wherein the device comprises two active electrode assemblies.

Typically, the therapeutic agent 51 will be dissolved in a therapeutic agent solution 54, also described as therapeutic agent composition 54 which is used to fill reservoir 21. In various embodiments solution 54 comprises an aqueous solution and will sometime be referred to herein as aqueous solution 54. In addition to therapeutic agent 51, solution 54 can include one or more pharmaceutical excipients 52 such as preservatives (e.g., citric acid) as is discussed in more detail below. The viscosity of solution 54 can be adjusted to have the solution readily wick from reservoir 21 into porous layer 24. Solution 54 can be preloaded into the reservoir 21 at the factory or can be added by medical personnel prior to use through means of a port 22, such as a self-sealing port (allowing injection of liquid through the port) which is coupled to reservoir 21 via means of a channel 27 as is shown in the embodiment of FIG. 3b. Suitable therapeutic agents 51 can include, without limitation, nicotine compounds for the treatment of nicotine cravings from smoking or other tobacco addition; methadone compounds for the treatment of heroin (or other opioid) cravings and withdrawal symptoms from heroin addiction and one or more of Acetylcysteine, Baclofen, Bupropion, Vanoxerine, and Vigabatrin for the treatment of cocaine cravings and withdrawal resulting from cocaine addiction. Other therapeutic agents 51 for the treatment of craving and withdrawal from other chemical dependent addictions are also contemplated. Still other therapeutic agents 51 can include ferric pyrophosphate or other iron containing compound for the treatment of iron deficient anemia, insulin or various glucagon like peptides for treatment of diabetes or other blood sugar regulation disorder, fentanyl or other opioid compound for pain management and various chemotherapeutic agents for the treatment of cancer.

The return electrode assembly 30 comprises a tissue contacting conductive layer 34, an adhesive layer 35 and a connector 26 for coupling the electrode assembly to the electrical power source. In many embodiments, the return electrode assembly 30 can have substantially the same elemental configuration as active electrode assembly 20 (e.g., a reservoir 21, conductive tissue contacting layer 24) so as to function as an active electrode assembly as is shown in the embodiment of FIG. 3b.

In many embodiments, patch 15 also includes one or more pair of electrodes known as lateral electrodes 40. Lateral electrodes 40 are placed on either side of porous portion 24 at a selectable distance from the perimeter 24p of porous portion 24 as is shown in the embodiments of FIGS. 3a-3b and 4a-4b. Lateral electrodes 40 can comprise various conductive materials including metals, graphite, silver chloride and other like materials. In various embodiments, all or a portion of lateral electrode 40 can include an insulative coating so as to be a capacitively coupled electrode that delivers current to the skin via capacitive coupling. Lateral electrodes 40 are also electrically isolated from electrodes 20 and 30 and will typically include their own wave form generator circuits.

The lateral electrodes 40 are arranged with respect to porous portion 24 such that they result in a conductive pathway 104 which goes through the skin S underlying portion 24 and is substantially parallel to the skin. Embodiments of patch 15 that employ lateral electrodes 40 with delivery electrodes 20, allow for the flow of two currents, a first current 60 and a second current 70. First current, 60 flows between electrodes 20 and 30 and serves to provide an electromotive force which acts to drive the therapeutic agent 51 into and across the layers of the skin S. The second current 70, known as sieving current 70, provides an electromotive force that acts on the therapeutic agent 51 in a direction parallel to the skin S so as to cause oscillation of therapeutic agent 51 in a direction parallel to skin S. This oscillation acts to sieve the therapeutic agent through pathways of lesser or least diffusional resistance in the skin. For embodiments where second patch 15" contains lateral electrodes 40 and is used to deliver therapeutic agent, a third current 70' can be delivered from lateral electrodes on the second patch 15" to also create an electromotive driving force to oscillate the therapeutic agent substantially parallel to the skin surface underneath the second patch 15". Further description of the arrangement and use of lateral electrodes 40, including their use in generating a sieving current, is found in U.S. patent application Ser. No. 12/658,637, filed Feb. 10, 2010 which is incorporated by reference herein in its entirety.

Referring now to FIGS. 5a-5d, various embodiments of the invention for use in on demand transdermal delivery of a therapeutic agent will now be described. Such embodiments include systems 5' and methods for on demand delivery of therapeutic agents 51. As used herein, the term "on demand"; refers to the ability of the patient or other person (e.g., a medical care provider) to initiate the delivery of therapeutic agent. This includes the initiation of a therapeutic agent delivery period and/or cycle of therapeutic agent delivery periods described below. The initiation of any of these can be a signal/input from a patient activation device such as a push button device and/or a signal received from a wireless device such as cell phone or other RF-enabled device. Such "on demand" embodiments provide for one or more of the following: i) the ability for the patient, other user or a controller/machine to initiate the delivery of therapeutic agent 51 to the patient; and ii) the ability to stop or otherwise limit the passive diffusion of therapeutic agent 51 during periods of time when an iontophoretic current is not supplied to patch assembly 15cp. In many embodiments, on demand transdermal delivery can be implemented by use of a biphasic transdermal iontophoretic delivery system 5" (biphasic transdermal iontophoretic delivery is defined and further described below). Such embodiments are particularly useful for the delivery of therapeutic agents 51p (herein after medication 51p) for the treatment of addictive cravings, such as nicotine or other nicotine compound for the treatment of cravings (e.g., for cigarettes) from tobacco addiction. However, it should be appreciated that embodiments of such a system 5" can be used for the delivery of any therapeutic agent 51 described herein or known in the art for the treatment of any number of conditions.

Referring now to FIG. 5a an embodiment of an "on demand" transdermal delivery system 5' will now be described. The system may be configured for on demand delivery of therapeutic agent 51 by the patient and/or a medical care provider. System 5' may also be configured as a biphasic transdermal iontophoretic delivery system 5" described herein, for example, through the use of a control program 93p described below. The system 5' includes a patch assembly 15cp including a patch 15, electrodes 14, therapeutic agent reservoir 21 and electronic module or section 90 including a user activated device 91 (also referred to as activation device 91) for allowing the patient or other user to initiate delivery of therapeutic agent 51. Electrodes 14 will typically include a delivery or active electrode 20 and a return electrode 30 as described herein. Active electrode 20 is configured to be in fluidic communication with a therapeutic agent reservoir 21 for storing a supply of therapeutic agent 51. As described herein, in many embodiments, therapeutic agent 51 will be dissolved in a solution 54 (contained in reservoir 21) so as to be in ionic form. According to one or more embodiments, solution 54 containing therapeutic agent 51 can be loaded into reservoir 21 at the factory and/or at the pharmacy by a pharmacist before pickup by the patient. According to other embodiments, therapeutic agent 51 is stored in reservoir 21 in solid form and liquid comprising solution 54 is added to the reservoir by the user or medical care provider immediately prior to use.

In various embodiments, patch 15 can have a substantial oval shape 15o including, for example, peanut or cassini-shaped ovals 15oc having side portions 15s and a tapered center portion 15c as is shown in the embodiment of FIG. 5a. Electrodes 14 including active electrode 20 and return electrode 30 can be positioned in side portions 15s and an electronics module 90 positioned in the center portion 15c.

Figure 6A:
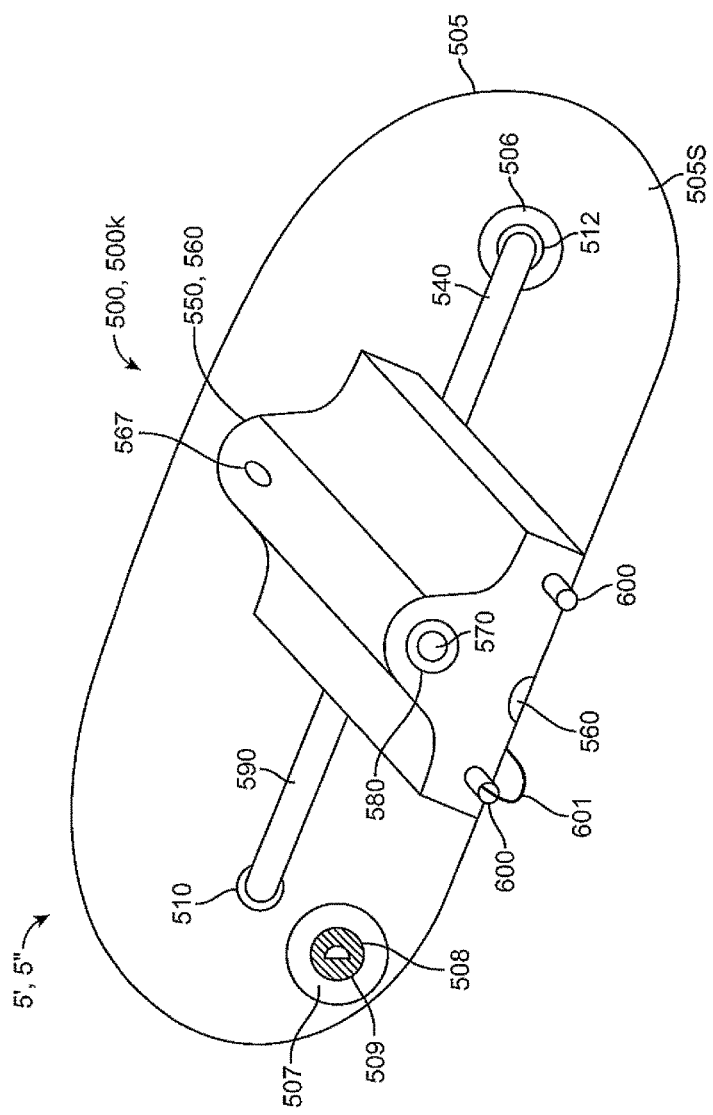
FIGS. 6a and 6b are perspective views showing an embodiment of a system/patch assembly for iontophoretic transdermal delivery of a therapeutic agent (such as a nicotine compound for the treatment of nicotine cravings from tobacco use) including a patch and an electronics assembly.
Figure 6B:
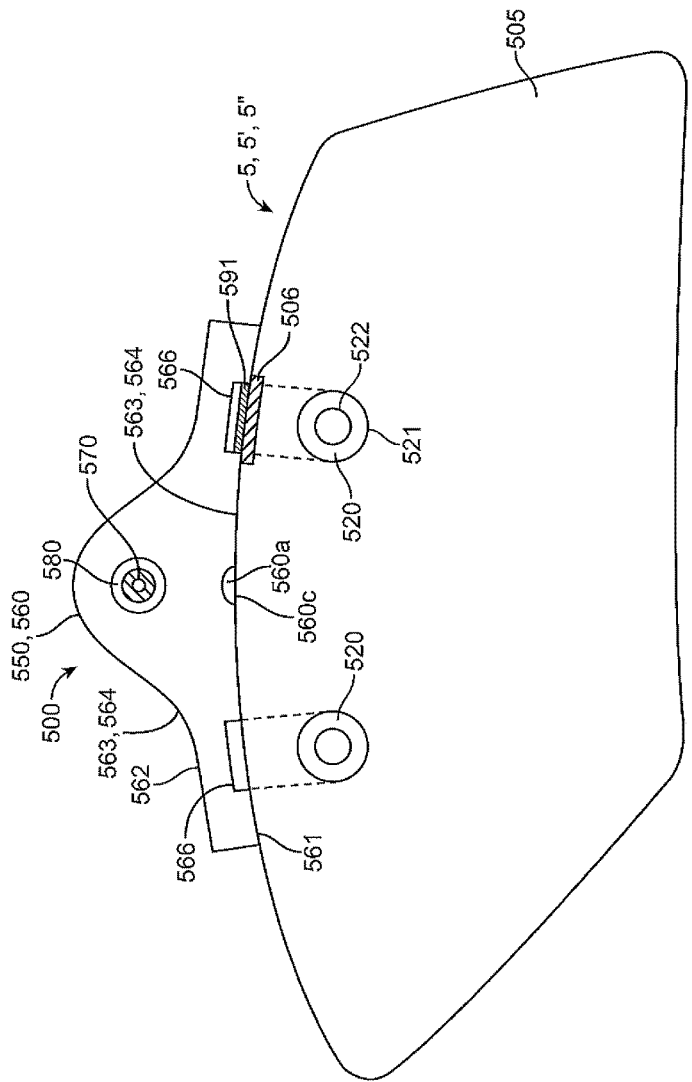
Figure 6C:
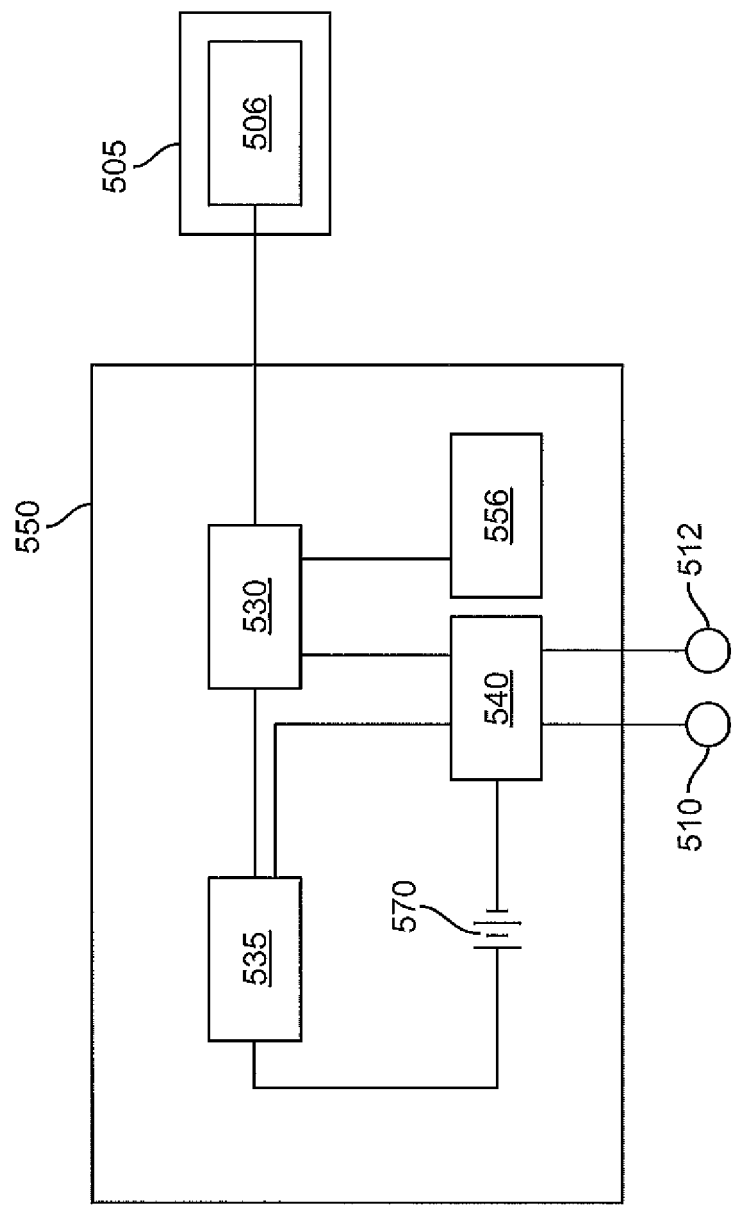
FIG. 6c is a block diagram of an embodiment of the electronics assembly including a controller, current source and current switching device.
Figure 7A:
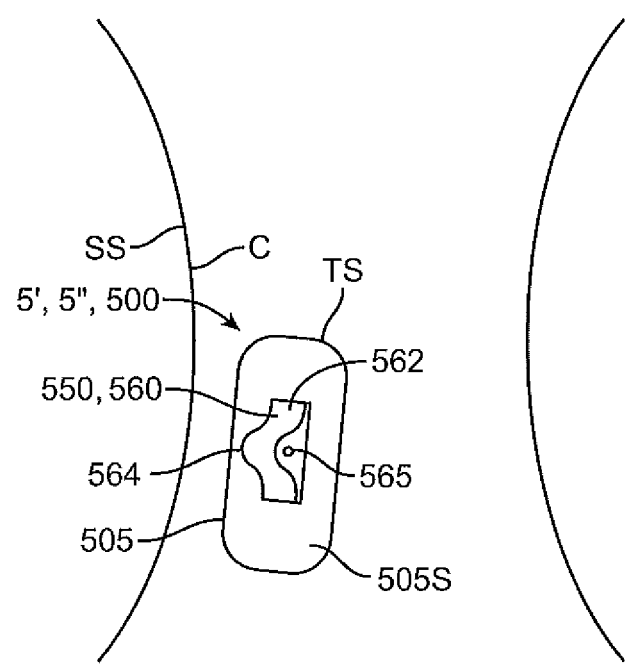
FIG. 7a is a perspective view showing placement of the embodiment of FIGS. 6a and 6b on an example site on the skin of a user.
Figure 7B:
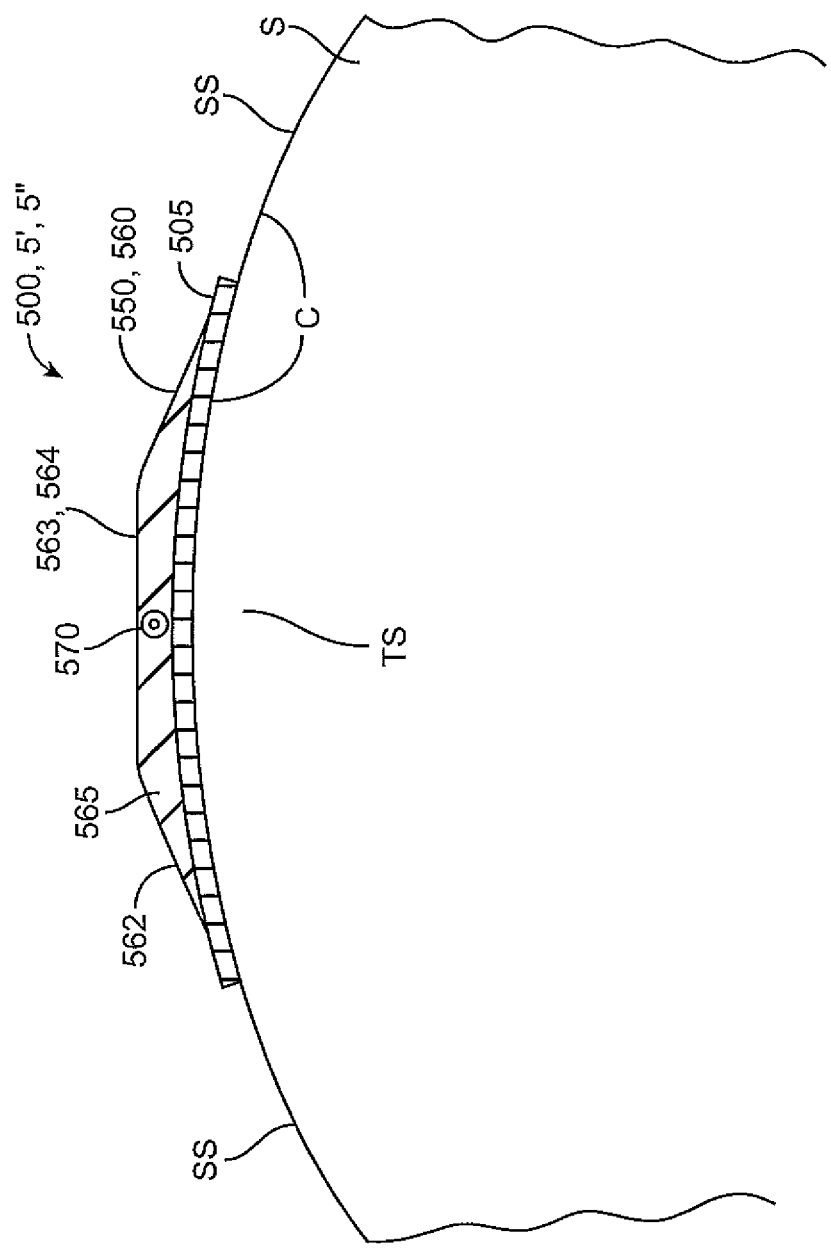
FIG. 7b is a lateral view showing an embodiment of a patch assembly having a curved contour positioned at a tissue site having a curved contour.

Electrodes 20 and 30 are positioned on opposite side portions 15s as is shown in the embodiment of FIG. 5a; however other configurations are also contemplated such as the placement of electrodes 20 and 30 in each side portion 15s. Electronics module 90 can include a controller 93 which may correspond to controller 530 (shown in FIG. 6c) and a power source 97 which may correspond to power source 570 (shown in FIG. 6b) and can include an electrochemical storage battery and circuitry for converting a DC (direct current) signal from the battery(s) into an AC (alternating current) signal. The electronics module 90 includes a user activation device 91 such as a push-button or switch for initiating a drug delivery cycle to deliver a dose of an opioid or other therapeutic agent 51 (e.g., an antiemetics). Other electromechanical activation devices 91 known in the art are also contemplated. Typically, activation device 91 is coupled to controller 93 (or other controller) so that signals 91s generated by device 91 provide an input to the controller for initiating a function such as initiation of a delivery period and/or delivery cycle of therapeutic agent 51. However, in additional or alternative embodiments, activation device 91 may comprise an externally connected device such as a push-button device that is electrically connected to module 90 (e.g., by a wire) and positioned and configured for easy access by the patient (e.g., a device that is attached to the patient belt or may lie by the patent's bed side). In still other embodiments, activation device 91 may comprise a wireless device, such as a cell phone, pda or RF-enabled communication device that can be carried, worn or placed in close proximity to the patient. For such wireless embodiments of device 91, device 91 and/or controller 93 may include various passwords or other codes to prevent accidental and/or other unauthorized use.

Referring now to FIGS. 5b-5d, embodiments of a method for "on demand" drug delivery using a biphasic transdermal iontophoretic delivery system 5" will now be described. Embodiments of this method are applicable with various embodiments of the patch and electrode assemblies described herein such as patch assembly 15cp and 500. "Biphasic transdermal iontophoretic delivery" refers to the use of a transdermal iontophoretic delivery system having a first and second phase of drug delivery. In some embodiments, the first and second phase of drug delivery may correspond to a delivery period and a non-delivery period. The delivery period in turn may correspond to a period of active transport of the therapeutic agent (e.g., using a drive current) and the non-delivery period to a period of active inhibition of such transport (e.g., using a holding current). As shown in FIGS. 5b-5d, before the initiation of a delivery cycle (e.g., by the patient, or other user) no or minimal agent is delivered as the agent is held within reservoir 21 by a holding current 320 described below. When the patient presses activation device 91 this generates a signal 300 which is fed into the controller 93. The controller 93 can include a control program or other logic 93p for starting a drug delivery period 340 upon receiving the signal 300. The control program 93p then initiates the beginning of a drug delivery period 340 by the flow of a first current known as a drug delivery current 310 (also referred to herein as a drive current 310) which has a polarity and magnitude or other characteristic configured to repel therapeutic agent 51 from the reservoir 21 and into the skin (the polarity being the same in sign (i.e., positive or negative) to the charge to that of the ionic form of therapeutic agent 51). The other characteristics of current 310 can include, without limitation one or more of the voltage, frequency/period or shape of the waveform of current 310 (these characteristics can also be used for adjustment of holding current 320 to perform its function).

Controller 93 keeps the delivery current 310 on for the delivery period 340 to deliver a selected dose of the therapeutic agent 51 into the skin as shown by the delivery curve 350 (also referred to as delivery profile) in FIG. 5d (the delivery period and delivery current can be stored in controller 93 and/or determined by program 93p, for example, using the transfer function and other modeling methods described in the appended example). At the end of the delivery period 340, the controller stops the delivery current 310 and starts a non-delivery period 330 (also described herein as refractory period 330) by generating a holding current 320. Holding current 320 has a polarity and magnitude or other characteristic configured to retain agent 51 within reservoir 21 by the force of electrostatic attraction (e.g., the polarity of the holding current 320 has the opposite sign as the charge of the ionic form of the therapeutic agent) so as to prevent or minimize passive diffusion of the therapeutic agent from the patch into the skin. Such minimal diffusion is shown in the non-delivery curve 360 in FIG. 5d. Such passive diffusion would otherwise occur without the presence of attractive force from the holding current 320. In particular embodiments, one or more characteristics of holding current 320 can be adjusted relative to the type and concentration of the therapeutic agent 51 within solution 54 and/or other property of solution 54 so as to assure that the holding current is sufficient to retain agent 51 within reservoir 21. For example, the magnitude of the current 320 can be proportionally or otherwise adjusted (e.g., geometrically) relative to the concentration of therapeutic agent 51 within solution 54. For embodiments delivering various nicotine salts described herein, holding current 320 can also be adjusted depending upon the particular nicotine salt and its concentration within solution 54. The current may be increased proportionally or in another fashion relative to the concentration of the nicotine salt. The adjustment can be done at the factory, by the medical caregiver, pharmacist (e.g., when they mix up a particular nicotine salt into solution 54) or via software within controller 93. The adjustments can also be done dynamically over the course of a delivery cycle to account for changes in the concentration of agent 51 within solution 54. In particular embodiments, a sensor may be employed to measure the concentration of agent 51 within solution 54 within output of the sensor being fed as an input to controller 93. In related embodiments similar adjustments can be in the characteristics of current 310 relative to the concentration of agent 51 in solution 54 or other property of solution 54 so as to assure that sufficient agent 51 is delivered out of reservoir 21 and into the patient's skin.

Also, during non-delivery period 330, the controller locks out or otherwise prevents the start of another delivery period so as to prevent the patient (or other person) from repetitively dosing themselves and thus over-dosing themselves. After the lockout period, the controller then allows the start of another delivery cycle. The controller can also be programmed or otherwise configured to only allow a maximum number of administered doses of agent 51 over a selected period of time, for example, 12, 24 hours etc. In particular embodiments for the delivery of therapeutic agents 51p for the treatment of addiction and addictive cravings, such as nicotine compounds for the treatment of nicotine cravings, the maximum number of doses can correspond to 24, 40, 48, 60, 80, 98 or 100 doses over a 12 or 24 hour period. The maximum number of doses is configured to keep the concentration (e.g., plasma concentration) of therapeutic agent within a therapeutic index (known in the art) and prevent the dose from exceeding a maximum tolerated dose such as that which would cause or begin to cause respiratory depression, low blood pressure, slowed or fast heart rate and/or other adverse physiologic affects. Similarly, the maximum number of delivered doses and/or lockout period can be selected to keep the rate of delivery of therapeutic agent 51 to the patient below that which would cause such adverse affects. The maximum number of doses and lockout period can be determined based on one or more parameters including without limitation, the therapeutic agent, the patient's age and weight, their condition and other therapeutic agents they are receiving (currently, previously or in the future).

Referring now to FIGS. 6a, 6b, 6c, 7a and 7b, in various embodiments, a system 500 for iontophoretic transdermal delivery of therapeutics agents 51p for the treatment of addictive cravings and/or other therapeutic agents can comprise a skin conformable patch 505 and an electronics assembly 550. System 500 (also described herein as patch assembly 500) can be configured as an "on demand" transdermal delivery system 5' and/or biphasic transdermal iontophoretic delivery system 5" as described herein. Patch 505 includes first and second electrode assemblies 510 and 512 which can correspond to one or more embodiments of electrode assemblies described herein. The materials used to fabricate the electrode portions of the assemblies can include various corrosion resistant materials such as graphite further described in U.S. patent application Ser. No. 12/824,146 and Ser. No. 12/824,147 (both filed Jun. 10, 2010) which are fully incorporated by reference herein for all purposes. Also, one or both of electrode assemblies 510 and 512 can include a pair 520 of tissue contacting ring shaped electrodes 521 and 522 concentrically spaced or otherwise arranged to reduce edge effects as is further described in U.S. patent application Ser. No. 12/832,011 (filed Jul. 7, 2010) which is fully incorporated by reference herein for all purposes.

Electronics assembly 550 typically includes a housing 560 which engages patch 505 so as to form patch assembly 500. Housing 560 includes a bottom and top surface 561 and 562 respectively, with the bottom surface 561 typically being the area of contact for engaging patch 505, though other arrangements are also contemplated. In particular embodiments, the housing 560 can be configured to be detachably coupled to patch 505 via one or more detachment elements 600.

Housing 560 can have a variety of shapes. In many embodiments, it can include a shaped contour 563 such as a curved shaped contour 564 (which can be for one or both of bottom surface 561 and top surface 562) that is configured to correspond to the contour C of the skin surface SS at the target tissue site TS where patch assembly 500 is placed such as the contour of the patient's arm, leg or abdomen (e.g., on the front or side of the stomach including below the waist line so as to not be visible). Contours 563 and 564 may: i) correspond to a standard contour for a particular target site TS; ii) may come in different sizes and shapes for different target tissue sites and sizes of patients; or iii) may be custom shaped for the particular patient and target tissue site. Also, the housing 560 can be conformable so as to at least partially conform to the contour C of the skin surface SS at the target tissue site TS where the patch 505 and housing 560 are placed (both when the patient is still and when they are moving resulting in bending movement and other deformation of the skin such that the skin surface contour is a flexing contour). Accordingly, in various embodiments, all or a portion of housing 560 can comprise various flexible polymers known in the art such as various elastomeric polymers, e.g., silicone and polyurethane. Other flexible polymers are also contemplated. The flexibility/conformability of the housing can also be configured to vary over the length of the housing to meet the needs of the particular target tissue site TS. For example, the housing 560 can be configured to have the greatest amount of flexibility at its center portions 560c (which can be achieved in some embodiments by putting a crimp or articulated zone 560a near the center of the housing). Also, the flexibility profile of the housing 560 can be matched or otherwise correlated to the shape and flexibility profile of the patch 505. For example, in particular embodiments, the flexibility/conformability of the housing can be configured for embodiments of the patch 505 having ring shaped electrodes 521 and 522. In these and related embodiments, housing 560 may have a structure which include areas 566 of greater flexibility (e.g., less stiffness) which may approximately align with ring shaped electrodes 521 and 522 (or others) such that the overall flexibility of the assembly 500 is not decreased over these areas. Areas 566 can have a shape which corresponds to the shape of electrodes 521 and 522 (or other shaped electrodes), though the size of the areas can be different from the size of the electrodes. Areas 566 can be achieved by decreasing the thickness of the housing in these areas and/or the use of more flexible materials. Other structures for housing 560 including shaped areas 566 are also contemplated, such as structures which have oval shapes areas 566 or even recessed areas 566.

Also in various embodiments, housing 560 cannot only be conformable, but also have a profile 565 shaped and sized such that the entire patch assembly 500 can be worn beneath the user's clothing and can bend and flex sufficiently so that: i) it is not readily detached by pressure or force from the user's clothing (due to movement of the clothes and/or skin), allowing the patch assembly 500 to stay on for extended periods when adhered to a tissue site underneath the user's clothes; and ii) is not readily visible beneath the user's clothes. In various embodiments, the profile 565 of the housing can have a contour 564 (of one or both of top and bottom surfaces 562 and 561) which corresponds to the contour C of the surface of the patient's arm, leg, abdomen or other target tissue site TS. Further, embodiments of the housing 560 can be sized, shaped and otherwise fabricated to bend and flex sufficiently to account for movement of the patient's skin when the patch assembly 500 is placed on the patient's abdomen, arm, leg and other target tissue sites. In this way, even when the patch assembly 500 is placed under clothes (or not), the assembly can remain sufficiently adhered/attached to the patient's skin for an extended period of time so as to allow a desired dose of the drug or other therapeutic agent 51 to be delivered. In various embodiments, the time period can be up to 24 hours, up to three days, up to a week with even longer periods contemplated. Specific combinations of a patch 505 and housing 560 can be configured for specific desired attachment periods using one or more factors described herein (e.g., flexibility surface area, etc.). For embodiments of the patch including elemental iron, such configurations can allow the patch to remain sufficiently adhered to the patient's skin for a sufficient time to deliver a therapeutic dose of the desired therapeutic agent 51 such as an agent 51p for the treatment of the particular addictive craving (e.g., nicotine for the treatment of nicotine craving from smoking or other tobacco addition). Similar configurations and methods can be employed for delivery of other drugs and therapeutic agents described.

Further, one or more of the size and shape (e.g., shape of the housing bottom surface 561 such as oval, circular, dogbone etc.) and flexibility of the housing 560 can be selected relative to one or more of the size and shape (e.g., shape of patch surface 505s) and flexibility of patch 505 such that when the patch assembly 500 is worn openly or beneath the patient's clothes, the applied amount of force from the housing 560 to the skin surface SS beneath the patch (due to movement of the patient's skin) or the clothing to the skin surface beneath the patch 505 (due to movement of the clothing or skin) is fairly uniform (e.g., there is a substantially uniform force distribution with minimal areas of force concentration). In use, these and related embodiments serve to minimize the amount of thermal, electrical or other injury to the skin from high current densities and/or hot spots from such force concentrations. Additionally for embodiments using delivery of therapeutic agent(s) 51 from embodiments of patch 505 having two more or electrode assemblies (e.g., assemblies 510 and 512) such configurations minimizing force concentrations (from skin movement etc.) also serve to minimize any effect on the delivery of therapeutic agent from the first electrode relative to the second electrode (or others). In particular embodiments, this can serve to minimize any effect on the delivery rate or total delivered amount of therapeutic agent from the first electrode assembly 510 relative to the second electrode assembly 512 (or other electrode assemblies).

In particular embodiments, such results can be achieved by matching the flexibility of the housing 560 to the patch 505 (either approximately equivalent or a selected amount higher or lower, e.g., 5 to 50%) as well as configuring the surface area of the patch 505 to be large enough relative to the surface area of the housing 560 so as produce a snow-shoe like effect so as to evenly distribute any applied force to the housing from clothing or other applied force (such as that due to movement of the skin) over the entire surface area of the patch 505. Surface area ratios in the range of 1:1.5 to 1:10 (housing surface area to patch surface area) are contemplated, with specific embodiments of 1:2, 1:3, 1:5.

In still other embodiments, the housing 560 or patch 505 may include a pressures sensor 567, such as a solid state strain gauge which senses the amount of force applied by the user's clothes to the housing and/or patch. Input from the pressure sensor can then be used to modulate (either increase or decrease) current delivered to the patch relative to the applied force. The current can be modulated down to prevent the development of hot spots on the patch from excessive pressure or modulated up to account for any increase in the electrical impedance of the skin due to the applied pressure.

Assembly 550 will typically include a power source 570 (also referred to herein as current source 570) and a controller 530 (e.g., a microprocessor or like device) for controlling one or more aspects of the iontophoretic delivery of the agent to the skin. Controller 530 can also include an integrated or separate power controller 535 for controlling the delivery of current to the skin. One or both of the controllers 530 and 535 can be coupled to an H-bridge or other current switching/limiting device 540 for limiting or otherwise controlling the delivery of current to the skin. The housing will also typically include a cavity 580 for current source 570, such as a cylindrical shaped cavity which may be sized for standard size batteries such as AA or AAA batteries. Other shapes for cavity 580 are also contemplated.

In various embodiments, current source 570 can comprise one or more electrochemical batteries including an alkaline, lithium, lithium-ion and like chemistries. For ease of discussion, current source 570 will be referred to herein as battery 570 but other current sources are equally applicable. Battery 570 can also comprise a rechargeable battery known in the art. The battery 570 can have a selected capacity to deliver sufficient current/voltage to the skin for transdermal delivery of the therapeutic agent for periods ranging from 2 to 24 hours or even longer. Power source 570 may also correspond to alternating current power source. Accordingly, in embodiments including an electrochemical battery(s), power source 570 may include circuitry for converting a DC signal from the battery(s) into an AC signal. Other power/current sources 570 are also contemplated, such as various storage capacitors and piezo-electric based energy harvesting devices.

The patch 505 will typically include one or more conductive areas 506 for electrical coupling to conductive elements 591 on the electronics assembly 550. The conductive areas 506 can be coupled to conductive traces 590 placed on the patch surface 505s or within the patch 505. The conductive elements on the electronics assembly 550 can be coupled to one or both of controller 530 and current source 570.

Detachment elements 600 can be spring loaded and can be configured to be engaged by the fingers of a user. In particular embodiments, detachment elements 600 may include or be mechanically coupled to one or more anchoring elements 601 such as a hook for anchoring into patch 505. The anchoring elements 601 may also comprise adhesive areas placed on the housing bottom surface 561 which engage the patch surface 505S.

In use, detachment elements 600 allow the user to attach and detach an electronics assembly 550 to a selected patch 505. This allows the electronics assembly 550 to be reused for multiple patches. In an exemplary embodiment of using system 500, the user can obtain a particular patch 505, scan information about the patch using a bar code reader (or other indicia reading means) described below and then attach the patch 505 to the assembly 550. When the user is done using the patch (e.g., such as when the desired amount of drug has been delivered) the user then detaches assembly 550 from the patch 505 discarding patch 505. In particular embodiments, assembly 550 can include programming which provides a signal such as beep or other alarm indicating to the user when to remove the patch 505. As an alternative, the patch surface 505s can include an indicator portion 507 which changes color or otherwise provides visible indicia 508 to the user when the required amount of agent has been delivered to the skin. In one embodiment, the indicia 508 can comprise a symbol or marking 509 that becomes visible when the amount of therapeutic agent 51 has been delivered. Visibility of the marking can be due to depletion of therapeutic agent 51 within patch 505 and/or a chemical or electrochemical reaction within or on the patch.

In particular embodiments, the electronics assembly 550 can also include a bar code reader for reading a bar code printed on patch 505 for ascertaining various information about the patch 505 including for example, the type and amount of therapeutic agent 51 contained in the patch, a desired delivery regimen, lot numbers (of the patch 505 and the therapeutic agent 51) shelf life, expiration date and related information. In an additional or alternative embodiment, patch 505 may contain a memory device (e.g. an EEPROM and the like) 506 which contains similar information and is readable by electronics assembly 550 (e.g., by controller 530). Assembly 550 may also contain a memory device 556 for storing information (described above) which may be coupled to microcontroller 530. The information contained in memory device 556 (e.g., type, dose and lot number of therapeutic agent 51) can be entered at the factory and/or by the doctor or pharmacist. Also information entry can be done directly or over a network such as the internet or cellular phone network or other like network. Other indicia reading means, for reading/detecting other indicia of information about patch 505 are also contemplated. Such indicia reading means can include, without limitation, use of various RFID chips known in the art.

System 500 including patch 505 and assembly 550, can be sized and shaped to be placed in any number of locations on the patient's skin including the arm, leg or abdomen, back or other location. The particular material properties of the patch 505 and housing 560 (e.g., thickness, modulus of elasticity, bendability, etc.) can also be so selected to allow placement at the desired location. For example, more flexible material properties can be selected for placement of the system 500 over skin areas with greater amounts of bending by the user, such as the stomach. Also, patch 505 and assembly 550 can be packaged together, for example, as a kit 500k (which can include instructions for use) wherein the assembly 550 is matched to patch 505 in terms of size, current source, programming mechanical properties etc. Further, a given assembly 550 can be calibrated for such a group of patches 505 or patches 505 from a particular lot number. In such embodiments, multiple patches 505 can be included with a particular assembly 550. In use, this allows the patient to obtain a complete supply of patches to meet the delivery requirements for a particular therapeutic agent 51 over a period of days, weeks, or months. Further, the assembly 550 can be programmed such that when the patient is near the end of his or supply of patches 505, that the assembly will give the patient a message to purchase more patches. In related embodiments, the assembly 550 can be configured to interface with the Internet and/or a mobile communication device such as cell phone, to send a message to the patient's pharmacy and/or doctor to do one or more of the following: i) renew the patient's prescription for a particular therapeutic agent patch 505; ii) have an order for a supply of the therapeutic agent patch 505 ready for the patient's pick up at his or her drug store; and/or iii) ship an order for the therapeutic agent patch 505 to the patient's house.

Referring now to FIGS. 8A through 8F, a discussion will be presented of various waveforms 800 or current output variations (over time) and their characteristics which can be used to promote delivery or retention of one or more therapeutic agents 51. Embodiments of these waveforms can be used for embodiments of the invention having a single or two or more active electrodes 20. Numerous embodiments described herein provide for waveforms 800 that vary between a given polarity and zero, wherein at that polarity, the current (e.g., current 310) causes the therapeutic agent 51 to be repelled into the skin. In other embodiments, the waveforms 800 alternate between positive and negative polarity such waveforms are referred to herein as waveforms 801.

For embodiments having a waveform 801 alternating between a positive and negative polarity, the waveform 801 can be a charged balanced waveform 802 configured such that the current delivered to each electrode assembly (e.g., assemblies 20 and 30) in use is a charged balanced AC current. A charged balance AC current means over a given duration, the amount of current delivered to the skin at each polarity is substantially equivalent. As used herein substantially equivalent means that two values are within 80% of one another, and more preferably within 90% or 99% over the period of one or more waveforms. By orienting the waveform to alternate in a charged-balance fashion, electrical toxicity or other damage to the skin can be reduced or minimized. In other embodiments, an alternating current waveform is used that is oriented towards being balanced in charge, but some asymmetry may exist.

Embodiments of waveforms 800 described below are variable between a minimum and maximum value. Some embodiments of waveform 800, such as described with FIG. 8b, may alternate in charge value (i.e. include reverse polarity) such waveforms are referred to herein as alternating charge waveforms 801. In such embodiments, the current delivery may be balanced in charge so that waveform 801 is a charged balanced waveform 802 as described above.

Figure 8A:
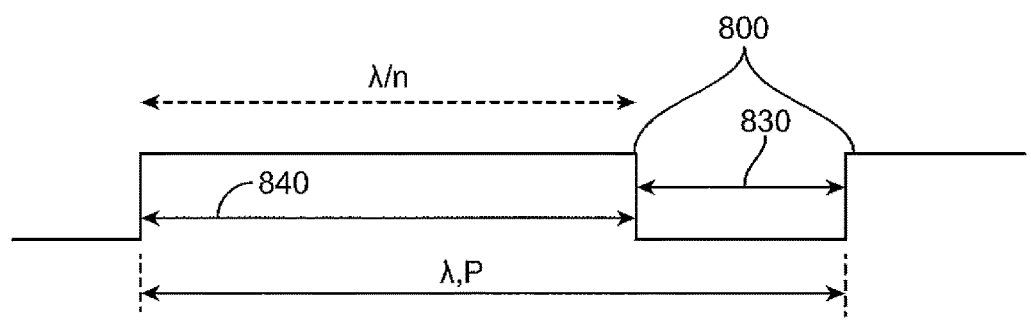
FIGS. 8a through 8f illustrate various waveforms or current output variations that can be used to promote various characteristics of embodiments of the transdermal iontophoretic delivery system.

FIG. 8a illustrates a waveform 800 that includes an extended or long drug delivery period or duration 840 (which may correspond to delivery period 340 shown in FIG. 5c), according to an embodiment. In some embodiments, the skin may be assumed to handle only a maximum amount of current in a given duration (maximum current delivery) (e.g. 80 milliamps per minute). For a given amperage, the duration of the output of an alternating power source (e.g., power source 100 described above) may be set so as to not exceed the maximum current delivery. The delivery duration 840 may be set to some portion or fraction (e.g. 50% for n=2) of the overall period of the current output $I_1$. For example, in some implementations, the maximum current delivery ($I_1$) is assumed to be 80 milliamps for one minute. In such an implementation, the delivery duration is set for 20 seconds on 4 milliamp output. Rather than switch to negative polarity, the output of the power source 100 may alternate to no amperage output (rather than switch polarity). While the waveform 800 depicted in FIG. 8A is rectangular, various embodiments of waveforms 800 may have alternative shapes (e.g. sinusoidal, trapezoidal), with the current delivery corresponding to the area under the curve. In the example shown by FIG. 8A, an alternating power source 100 initiates a delivery duration 840 on one electrode (e.g., active electrode 20), with delivery durations being set by a current that has a polarity that matches that of the charge of the therapeutic agent. The current may alternate to zero output, in which the drug delivery is substantially ceased. Thus, the non-delivery duration 830 may coincide with no current output, rather than reverse current. In other embodiments, non-delivery duration 830 is achieved through the use of a current which has a polarity which is opposite to the charge of active agent 51 as described below in the embodiment of FIG. 8b and above in the embodiment of FIG. 5b (e.g., in the form of holding current 320).

Figure 8B:
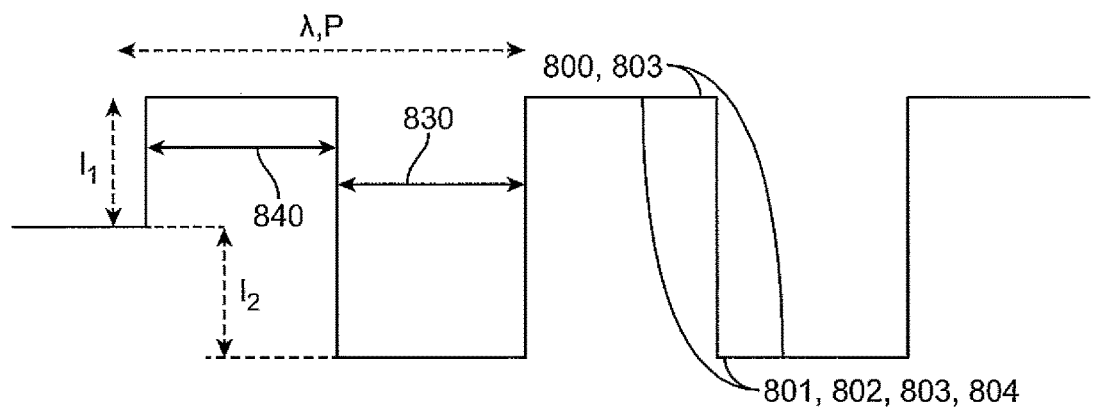

FIG. 8B illustrates another embodiment in which the alternating power signal outputs a symmetrical wave 803 such as symmetrical square wave 804. FIG. 8B (and other waveforms illustrated herein) illustrates use of charge balanced waveforms 802 to deliver charge balanced alternating currents. For example, symmetrical waveforms in polarity may be considered as charged balanced. Depending on the application, the period P of the cycle of waveform 802 may be long (e.g. 20 minutes) or short (1/60 seconds). The delivery duration 840 may correspond to half of the period P of the waveform 802. In the implementation shown, a reverse current is used in the non-delivery duration 830, to actively prevent agent delivery to the skin.

Figure 8C:
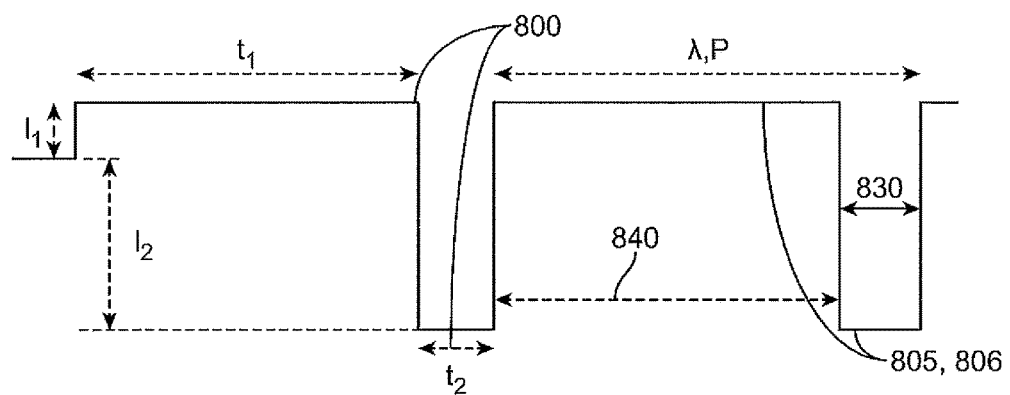

FIG. 8C illustrates another embodiment of the invention in which the alternating power signal outputs an asymmetrical wave 805 such as an asymmetrical square wave 806, in that the delivery duration 840 is different than the non-delivery duration 830. More specifically, the asymmetrical square wave 805 may include longer delivery durations ($t_1$), followed by short(er) rest durations ($t_2$). The rest durations may correspond to periods of no current, or as shown, reverse current ($I_2$). In one application, the rest duration enables the skin layer to recuperate from the drug delivery in the prior duration (e.g., to dissipate any heat, concentration of ions, or other by products resulting from the delivery of current). As an alternative or variation, the rest period may follow a period where no current is applied to the skin layer, so as to enable the skin layer to recuperate from application of current.

Figure 8D:
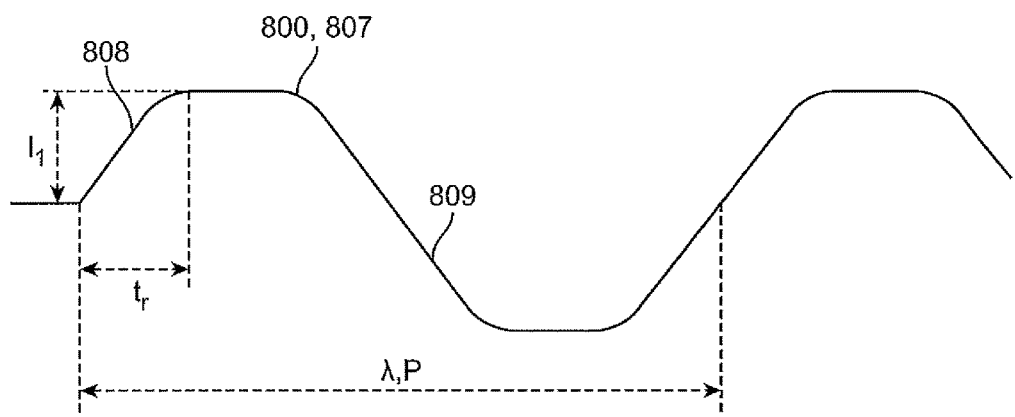

FIG. 8D illustrates another embodiment in which the alternating power signal has a trapezoidal waveform 807, so as to include ramp-up and/or ramp-down periods 808 and 809. As depicted, $I_1$ is the maximum current output generated from an alternating power source (e.g. power source 100). The ramp-up period 808 extends for a duration $t_r$, that is selected for reasons that include enabling the user to physically accustom to the application of current and/or delivery of therapeutic agent 51. The ramp-up period 808 may be long, to enable the ramp-up duration to be effective. In an embodiment, a ramp-down period 809 may optionally be implemented.

Figure 8E:
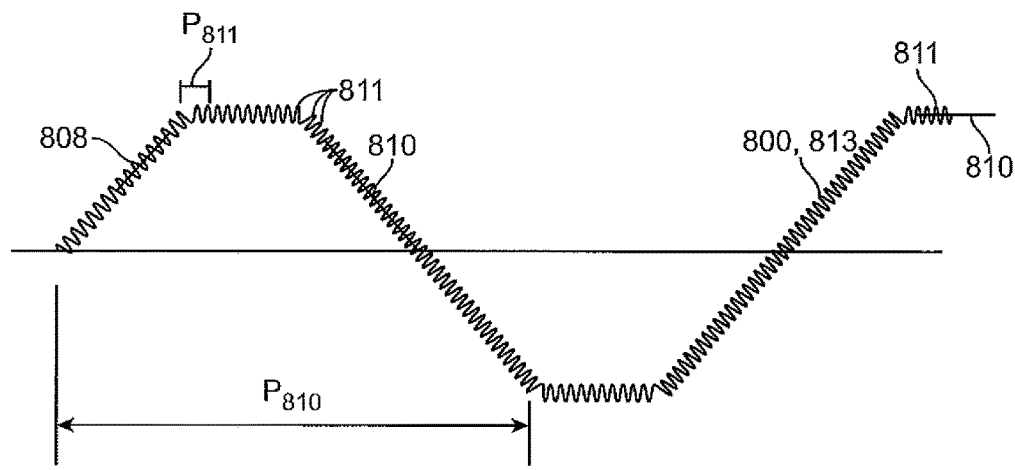
Figure 8F:
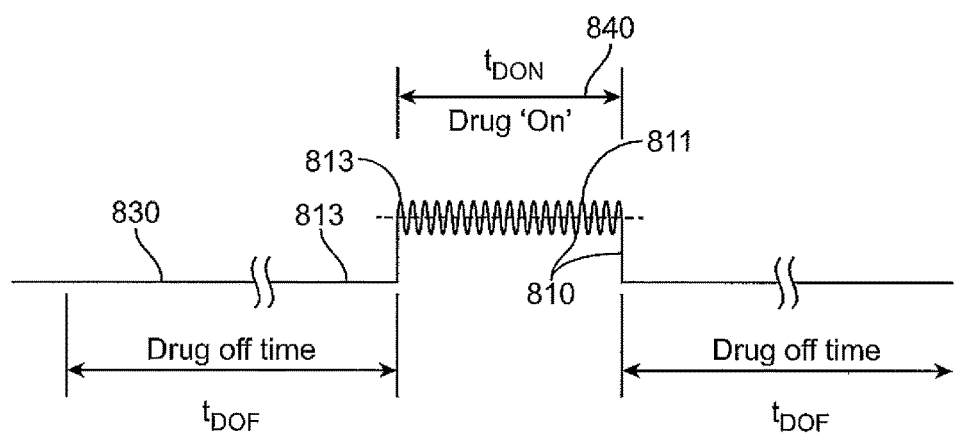

FIG. 8E and FIG. 8F illustrate alternative waveform variations including compound waveforms 813 in which high-frequency oscillations 811 are superimposed on a low frequency base waveform 810. The base waveform 810 may have a period $P_{810}$ that lasts seconds or minutes, corresponding to output current to the electrode assemblies ranging from a maximum (e.g., 4 mA) to no current and/or reverse current. The high-frequency oscillations reflect small variations in the current value at instances in the period. The period $P_{811}$ of the high-frequency oscillations 811 may be one or more magnitudes shorter than that of the base waveform. As an example, the base waveform 800 may have a period $P_{810}$ ranging from seconds to minutes, and the high-frequency oscillations of the waveform may have a period that ranges between milliseconds and seconds. The effect of the high-frequency oscillations 811 is to reduce the effects of the capacitive charge in the skin layer in receiving the therapeutic agent 51. The high frequency oscillations 811 may also be used to facilitate transport of the therapeutic agent through the skin including the stratum corneum by causing oscillations in the movement of the therapeutic agent as it travels through the skin so as to find pathways of least resistance through the skin. In such embodiments, the high frequency oscillations may be adjusted to enhance this effect through use of modeling (e.g., pharmacokinetic modeling) and/or the patient's age, skin type and skin location The base waveform 810 may be selected for considerations such as described in prior embodiments. For example, in FIG. 8E, the waveform 813 includes a ramp-up time period 808. In FIG. 8F, the waveform 800 has a delivery duration 840 that is switched to a non-delivery duration 830. An embodiment of FIG. 8F illustrates that the high-frequency oscillations 811 may be generated to be present only during the delivery duration 840.

Nicotine Applications

A discussion will now be presented on nicotine compounds which can be delivered using one more embodiments of the invention (e.g., various patch and electrode assemblies and systems described herein) and methods for the transdermal delivery of those compounds using those embodiments. The forms of nicotine which may be delivered by one or more embodiments of the invention include, without limitation, nicotine in its free base form, its analogues and derivatives as well as various salts of nicotine and analogues and derivatives of those salts. Nicotine and its analogues and derivatives as well as salts of nicotine will sometimes be referred to herein as nicotine compounds.

Nicotine Analogues

Nicotine analogues can include any substance having a nicotinergic effect (i.e. substances which bind to and/or have an effect on the nicotinic receptors, (specifically neuronal type nicotinic receptors) as is known in the art. Nicotine analogues can include without limitation, enantiomers and isomers of nicotine, substituted nicotines (Cl, Br, I, NO2, aryl, alkyl, etc.), oxidation products of nicotine, metabolic products of nicotine, compounds related to nicotine such as myosmine, nornicotine, anabasine, etc., and a variety of other compounds having either similar stereochemistry (conformation) and/or physiological activity. Further description of nicotine analogues including methods of their manufacture may be found in U.S. Pat. Nos. 4,590,278 and 5,138,062 which are incorporated by reference herein in their entirety.

Nicotine Salts

Exemplary pharmaceutically acceptable nicotine salts which can be delivered by various embodiments of the invention can include nicotine salts of the following: tartrate (e.g., nicotine tartrate and nicotine bitartrate) chloride (e.g., nicotine hydrochloride and nicotine dihydrochloride), sulfate, perchlorate, ascorbate, fumarate, citrate, malate, lactate, aspartate, salicylate, tosylate, zinc chloride, succinate, pyruvate, and the like; nicotine salt hydrates (e.g., nicotine zinc chloride monohydrate), and the like. Additional organic acids that can form salts with nicotine include without limitation, formic, acetic, propionic, isobutyric, butyric, alpha-methylbutyric, isovaleric, beta-methylvaleric, caproic, 2-furoic, phenylacetic, heptanoic, octanoic, nonanoic, oxalic, malonic, and glycolic acid, as well as other fatty acids having carbon chains of up to about 20 carbon atoms. Preferred nicotine salts include salts of hydrochloride, dihydrochloride, citrate, tartrate, hydrogen tartate, bitartrate, malate, salicylate and zinc chloride. Various embodiments of the invention also contemplate delivery of one or more of the above salts in which nicotine is substituted with either a derivative or analogue of nicotine. Further description of pharmaceutically acceptable nicotine salts may be found in U.S. Pat. No. 7,387,788 which is incorporated by reference herein in its entirety. Among other factors a particular nicotine salt may be selected based upon its solubility (e.g., higher vs. lower), its rate of active transdermal iontophoretic transport across the skin and its rate of passive transdermal diffusion across the skin. Solubility of the nicotine salt may be measured and/or determined from the Merk Manual or similar reference. The solubility may also be adjusted using one or more buffering agent, antioxidants (e.g., citric acid) or excipients described herein. Rates of active transdermal diffusion and passive transdermal diffusion may be determined using the methods described in the Example Section appended hereto. Also such methods may be used to establish the drive current 310 and holding 320 for a particular nicotine salt or nicotine analogue salt.

Weight Percent of Nicotine Salts in Aqueous Solution

For various embodiments of the invention in which patch assembly 15cp comprises one or more nicotine salts (or salts of nicotine analogues) described above, those salts can be dissolved in an aqueous or other solution 54 (e.g., an aqueous alcohol solution) contained within reservoir 21 or other portion of patch assembly 15cp. The dissolved nicotine salt content of solids in the aqueous solution 54 can range from about 1 to 50 weight (wt) %. In specific embodiments, the dissolved nicotine salt content is about 10 wt %, preferably above 10 wt %, preferably above 15 wt %, preferably from about 15 wt % to 30 wt %, more preferably above 20 wt %, more preferably from 20 wt % to 30 wt %. The specific wt % can be adjusted based on one or more of the following factors: tissue contacting area of the patch assembly 15$cp$, desired nicotine dose during a given delivery period (e.g., 0.5 to 3 mg), desired nicotine dose flux (e.g., mg/sec/cm$^2$ patch surface area), desired plasma concentration (e.g., desired nicotine plasma concentration (e.g., about 2 to 20 ng/(ml plasma, more preferably about 2 to 10 ng/ml), and total number of doses to be delivered by a given patch assembly (e.g., 10, 20, 40, 50 etc.). Dose response curves may be used to adjust the weight percent of nicotine salt based on more on more of these factors as well as for patient characteristics such as patient weight current cigarette use, physiologic measurement of the patient's current level of habituation to nicotine, etc.

Use of Pharmaceutical Excipients

In various embodiments the aqueous solution 54 may also one or more pharmaceutical excipients to perform one or more functions. Such excipients can include for example a buffering agent to maintain the pH of solution in the physiological range of that found in skin so as to reduce any skin irritation from the nicotine salt or other nicotine compound within the aqueous solution and/or to reduce any skin irritation as result of ionotophoresis. The buffering agent has sufficient buffering capacity and concentration in the solution and buffering properties to maintain the pH of the aqueous solution 54 in the range of 4 to 6, more preferably in the range of 4.5 to 5.5 and most preferably in the range of 4.6 to 4.8 as the natural pH of unwashed human skin has been reported to be 4.7. Suitable buffering agents can include organic and non-organic buffering agents. Exemplary inorganic buffering agents include, but are not limited to, phosphate buffer solutions, carbonate buffers, citrate buffers, phosphate buffers, acetate buffers, sodium hydroxide, hydrochloric acid. Exemplary organic buffering agents include, but are not limited to, lactic acid, tartaric acid, meglumine, monoethanolamine, diethylamine, triethylamine, diisopropylamine, aminomethylamine, trihydroxymethylaminomethane, tetrahydroxypropylethylenediamine. Other excipients may include a skin permeability enhancer to improve the permeability of the skin to various nicotine compounds, antioxidants to improve shelf life of the aqueous solution 54. Further description of various skin permeability enhancers and antioxidants as well as other excipients which may be used in the aqueous solution 54 (e.g., various gelling agents) or other portion of patch assembly 15$cp$ may be found in U.S. Pat. No. 7,387,788.

Use of Hydrophilic Polymer Matrices

In some embodiments, the aqueous or other solution 54 is contained within a hydrophilic polymer matrix such as a hydrogel matrix. The hydrogel matrix may be contained in reservoir 21, tissue contacting layer 24 or other portion of an electrode/patch assembly such as assemblies 14 and 15$cp$ described herein. The nicotine (or analogue or derivative) salt-containing hydrogel can suitably be made of any number of materials including a hydrophilic polymeric material, such as one that is polar in nature so as to enhance the stability of the dissolved nicotine compound. Suitable polar polymers for the hydrogel matrix comprise a variety of synthetic and naturally occurring polymeric materials. In one embodiment, the hydrogel formulation comprises a suitable hydrophilic polymer, a buffer, a humectant, a thickener, water and a water soluble nicotine or analogue or derivative salt. The suitable hydrophilic polymer may comprise a hydrophilic polymer matrix which in one or more embodiments may correspond to polyvinyl alcohol such as a washed and fully hydrolyzed polyvinyl alcohol (PVOH). A suitable buffer includes an ion exchange resin which is a copolymer of methacrylic acid and divinylbenzene in both an acid and salt form. One example of such a buffer is a mixture of Polacrilin (the copolymer of methacrylic acid and divinyl benzene available from Rohm & Haas, Philadelphia, Pa.) and the potassium salt thereof. A mixture of the acid and potassium salt forms of Polacrilin functions as a polymeric buffer to adjust the pH of the hydrogel to about pH 6. Use of a humectant in the hydrogel formulation is beneficial to inhibit the loss of moisture from the hydrogel. An example of a suitable humectant is guar gum. Thickeners are also beneficial in a hydrogel formulation. For example, a polyvinyl alcohol thickener such as hydroxypropyl methylcellulose aids in modifying the rheology of a hot polymer solution as it is dispensed into a mold or cavity. The hydroxypropyl methylcellulose increases in viscosity on cooling and significantly reduces the propensity of a cooled polymer solution to overfill the mold or cavity. In one embodiment, the nicotine (or an analogue or derivative) salt-containing hydrogel formulation comprises about 10 to 15 wt % polyvinyl alcohol, 0.1 to 0.4 wt % resin buffer, and about 1 to 2 wt % nicotine (or analogue or derivative) salt. The remainder is water and ingredients such as humectants, thickeners, etc.

Nicotine Dosages

Many embodiments of the invention are configured to deliver doses of a nicotine compound approximating the nicotine delivered by a single cigarette. Most cigarettes contain about 1 to 3 milligrams of nicotine in the smoke inhaled. According to one study, the average amount of nicotine delivered by a medium cigarette has about 1.1 mg (milligram) in a medium yield cigarette. Djordjevic M V et al. Doses of nicotine and lung carcinogens delivered to cigarette smokers. J Natl Cancer Inst. 2000 Jan. 19; 92 (2):106-11. The average dose delivered of nicotine per puff has been reported to be in the range of 0.08 to 0.12 mg. Accordingly, various embodiments of patch assembly 15$cp$ can be configured to deliver doses of nicotine or other nicotine compound in this range during a single delivery period with larger and smaller dosages contemplated. Further, the dose delivered during a delivery period together with the number of delivered doses during a delivery cycle can be configured to deliver between 0.7 to 3 mg of nicotine (or nicotine analog or derivative) during a delivery cycle with specific embodiments of 0.8, 0.9, 1.0 1.1, 1.2, 1.4, 2 and 2.5 mg of nicotine (or nicotine analog or derivative). As is discussed herein, both the dose delivered during a single delivery period and the total dose delivered during a delivery cycle can be adjusted for one or more patient characteristics and other factors described herein.

In various embodiments, suitable doses of nicotine (e.g., or nicotine analogue or derivative) for administration to a patient over a delivery period can include, for example, about 0.02 to 5 about milligrams, more preferably about 0.05 to about 2.5 milligrams, more preferably about 0.06 to about 2 milligrams, more preferably about 0.06 to 1 milligrams (mg), still more preferably 0.07 to 0.5 mg, and still more preferably 0.08 to 0.12 mg. Specific doses during a delivery period can include 0.08, 0.09. 0.10, 0.11 and 0.12 mg. For cigarette cessation applications, a more preferred dose delivered during a delivery period is about 0.1 milligrams of nicotine (or nicotine analogue) which corresponds to an average dose delivered from a single puff of a cigarette. This or other nicotine dose may be titrated for the patient's smoking pattern (e.g., long deep inhales (higher dose) vs. fast puff (lower dose), number of cigarettes smoked per day, e.g., 10 vs. 20), type of cigarette smoked (low vs., high nicotine), patient weight or other characteristic of the patient (e.g., age, etc.). Similar titrations may be done for other forms of inhaled tobacco use such as pipe or cigar use or even electronic cigarette use. Also, the delivered dose during a delivery period may be re-titrated based on the patient's progress in their smoking cessation plan as is discussed below.

In various embodiments, between about 1 to 80 doses of nicotine (or nicotine analogue) may be delivered over a 24 hour period; for example, 10, 20, 30, 40, 50, 60, 70 doses of nicotine can be delivered over a 24 hour period. Adjustment may be made for burst mode delivery as described herein. In one or more embodiments, a particular number of doses delivered in a set period such as a one hour, six hour, 12 hour or 24 hour period can be limited, for example, so as to not exceed a total delivered dose of nicotine or nicotine analogue. Accordingly in various embodiments, various lockouts may be programmed into system 5 and/or patch assembly 15cp to limit the number of doses and/or control the interval between doses (e.g., the non-delivery period).

Burst Mode Delivery of Nicotine Compounds

Figure 8I:
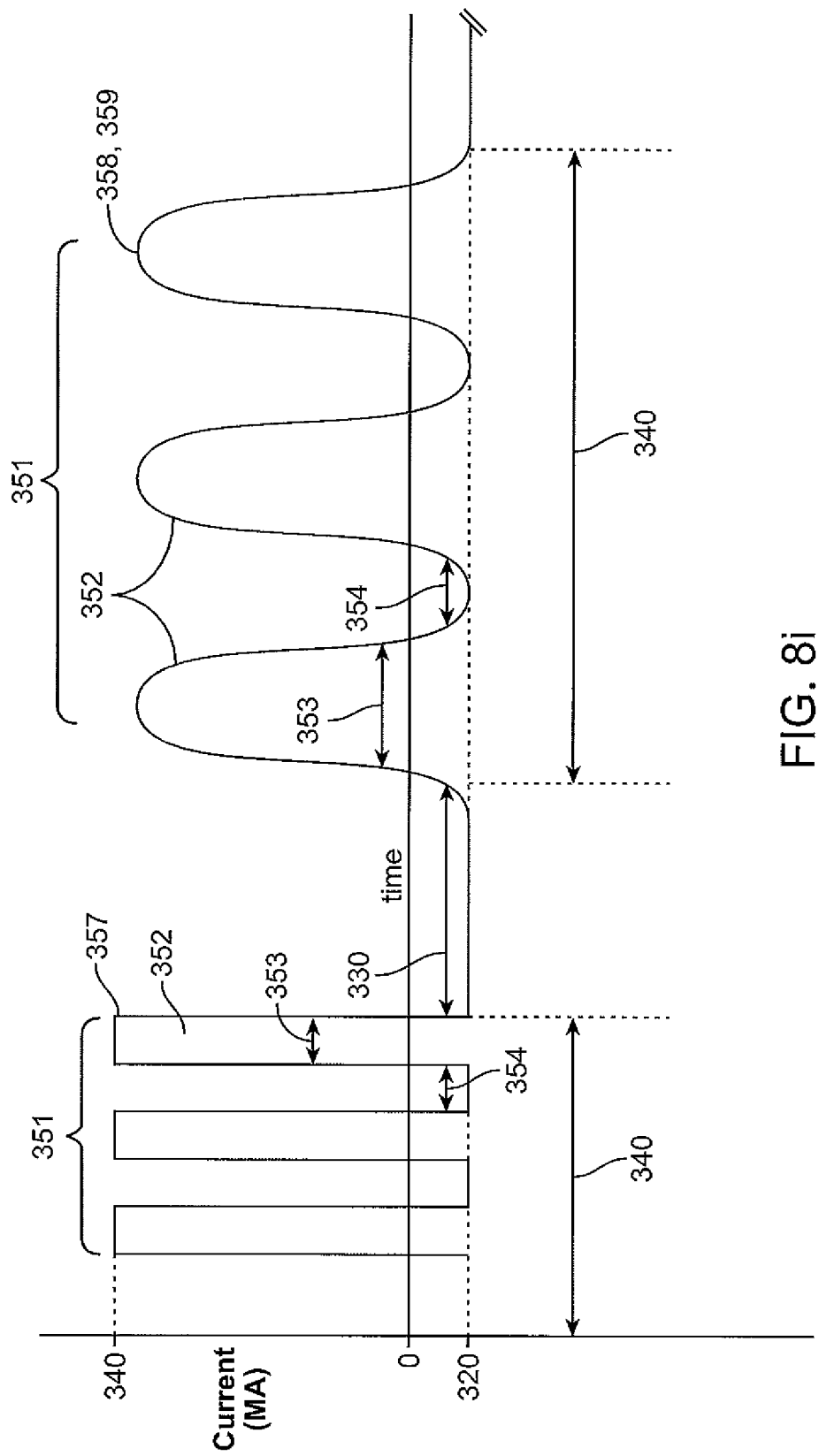
FIG. 8i illustrates different embodiments of burst mode delivery curves.

According to one or more embodiments of the invention the profile of the of dose of nicotine compound delivered during a delivery period and/or cycle (herein "delivery profile") can be configured to mimic or otherwise approximate the nicotine delivery profile 350a a patient experiences from smoking a cigarette or other form of tobacco use. In use, such an approach can reduce nicotine/cigarette cravings since the nicotine delivered during a delivery period/cycle mimics and/or more closely approximates that which the patient gets from the smoking of a cigarette (e.g., the profile from each puff of the cigarette) or other form of tobacco. Referring now to FIGS. 8g-8i, in many embodiments, for achieving such a mimicked delivery profile, the delivery curve or profile 350 for particular nicotine compound corresponds to a series of bursts 352 during a delivery period 340 resulting in a profile 350 corresponding to delivered profile 350a from smoking a cigarette or other inhaled form of tobacco as is shown in the embodiments of FIGS. 8g and 8h. Collectively, bursts 352 comprise a burst pattern 351. Delivery in such a fashion, is described herein as "burst mode" delivery. The duration 353 of each burst 352, interval 354 between bursts and delivered dose of nicotine compound for each burst may correspond to a puff duration 355, puff interval 356, puff nicotine dose for a particular patient so as to simulate a "puff to puff" delivery of nicotine to the patient. This may be done for a cigarette, cigar, pipe or an electronic cigarette. Typically, the bursts 352 may have a square wave shape 357, but they may also have a curve shaped 358 such as a half sign wave 359 as is shown in the embodiments of FIG. 8i. In various embodiments, the number of bursts may be between 1 to 30, 2 20 and 2 to 15. In specific embodiment the number of burst can be 2, 3, 4, 5, 6, 7, 8, 9, 10, 11, 12, 13, 14 and 15. In preferred embodiments, the number of burst corresponds to typical number of puffs taken by a patient and thus may have a range between about 8 to 12 bursts. As is described below, one or more burst parameters, such as duration of burst, interval between bursts and number of burst may be adjusted to reflect the smoking pattern of a particular patient as determined using one or more of the "smoking parameters" described herein. Other embodiments contemplate other delivery profile to mimic or otherwise simulate the nicotine delivery during a particular type of inhaled or other form of tobacco use. For example, a burst pattern 351 may be superimposed on a steady state delivery of nicotine compound during a delivery period 340. In various embodiments, the patent's plasma nicotine levels or other related measurement may be taken as the patient smokes a cigarette. According to one or more embodiments, the measurement can be made when the patient uses an electronic cigarette known in the art in order better control the precision of the nicotine dose delivered during each puff. The measurements can then be used to better approximate in profile 350 the actual delivery nicotine profile 350a for a given patient when they smoke a cigarette or use another form of tobacco.

Adjustment of Nicotine Delivery Parameters

As is discussed above, the dose of nicotine delivered during a delivery period can be adjusted based on one or more considerations described herein. In addition to this parameter, other parameters which may be adjusted in various embodiments of the invention can include the duration of a delivery period, the duration of non-delivery period. Further for embodiments using pulsed delivery of a nicotine compound, additional parameters which can be adjusted include, amount of nicotine delivered in a given pulse in a delivery period, the number of pulses in a delivery period. One or more of these parameters are referred to herein as the "nicotine delivery parameters" or "delivery parameters". In various embodiments, the adjustment to the delivery parameters can be made by the medical care provider, pharmacist or the patient. In particular embodiments to the delivery parameters can be made using various physiological measurements of the patient which are correlated to or otherwise indicative of the patient's current level of habituation to nicotine and/or the desire psychoactive effect. Such measurements include for example, heart, blood pressure, skin conductance/resistance. This allows the medical care provider to fine tune the delivered dose or other delivery parameter to reflect the patient's current use and/or psychoactive need for cigarettes or other inhaled nicotine product. This approach serves to decrease any feelings of nicotine withdrawal the patient may experience when they first stop smoking and switch to use of one or more embodiments of patch assemblies described herein. In use, this approach serves to increase a patient's compliance with the smoking cessation program since the patient doesn't go through any immediate nicotine withdrawal. Instead, the nicotine doses delivered to the patient can be gradually stepped down over a period of days, weeks or even months.

Embodiments Employing Adjustment in Delivery Parameters for Smoking Habits of the Patient Various embodiments of the invention also contemplate adjustment of a dose of delivered nicotine or other delivery parameter based on the smoking pattern and habits of the patient. A brief description will now be presented on those patterns. After a patient inhales smoke from a cigarette nicotine within the smoke is transferred from the alveolar sac of the lungs into the blood vessels surrounding the aveloli enriching the blood in those vessels with nicotine. The nicotine-rich blood then passes within seconds from the lungs to the brain where acts to produce two psychoactive effects: a stimulant and a relaxant depending in part on the concentration of nicotine in the blood. Smokers seeking a stimulating effect will take short quick puffs, which produced a low level of nicotine in the blood. Smokers wishing to relax will take deep puffs, which produce a higher level of blood nicotine. Thus, depending on the desired psychoactive effect, this can result in variation in one or more parameters (herein "smoking parameters") of the patient's smoking pattern. Such parameters can include, for example, the duration of each puff, puff volume, puff rate, the interval between puffs and total number of puffs. Values for a parameter will typically be considered to be average values determined by measurement and/or questioning of the patient. In this way, the delivery profile of nicotine compound delivered by embodiments of the invention can more closely approximate or mimic the nicotine delivery profile from the patient's actual use of cigarettes (or other form of inhaled tobacco). In use, this approach can reduce nicotine cravings since the nicotine delivered during a delivery period/cycle mimics (e.g., more closely approximates) that which the patient gets from the smoking of a cigarette or other form of tobacco. In particular embodiments a number of smoking parameters can be can be pooled together to model a smoking pattern to achieve a particular psychoactive effect desired by the patient. For example, puff duration, puff volume and puff rate can be pooled together in a model of a stimulant seeking vs. a relaxing seeking smoking pattern. The model can comprise a first, second order or other order polynomial equation, cubit spline etc. Each of the smoking parameters may comprise a coefficient of a particular order of the equation and may be weighted accordingly. Again in this way, by adjusting the delivered dose of nicotine to achieve a desired psychoactive effect of the patient, embodiments of the invention reduce nicotine cravings and other symptoms of withdrawal. This in turn, improves compliance with a smoking cessation program and reduces the potential for relapse upon completion.

Also for one or more embodiments using a pulsed delivery mode for nicotine compounds, the duration and number of pulses can be matched or otherwise correlated to the smoking pattern of the patient using one or more of the smoking pattern parameters. For example, according to one or more embodiments, the number of pulses can be matched or otherwise correlated (e.g., in rations of 1:2, 2:1 etc.) to the number of puffs by a patient as determined by measurement or questionnaire. According to other embodiments, more pulses having smaller amounts nicotine can be employed for patients smoking for a stimulating effect and fewer pulses having larger amounts of nicotine for patients smoking for a relaxing effect.

Embodiments Employing Adjustment in Delivery Parameters for Progress in Smoking Cessation Also, one or more of the dose delivered during a delivery period, duration of a delivery period or dose delivered during a delivery cycle (the "dose delivery parameters") may be reduced (herein the "reduction") over time so as to wean the patient from the nicotine craving and, consequently, aid the individual in ceasing smoking. The reduction can be made by the physician or other health care provider and can be made based on various factors including one or more of the following progress factors: i) how often the patient currently has nicotine cravings each day, ii) the decrease in the number of cravings from the start of their smoking cessation program and/or a prior adjustment period, iii) how many cigarette number of cigarettes they continue to smoke; and iv) the decrease in the number of cigarettes they smoke from the start of their smoking cessation program and/or a prior adjustment period. Using one or more of these four progress factors, the reduction in nicotine delivered can be titrated to the patient's individual progress in their smoking cessation program and in this way, facilitate a faster and more successful smoking cessation program (e.g., where they have greater success in kicking the habit not just at the end of the program but for extended periods there afterwards). The reduction can also be based on various physiologic measurements correlated to or otherwise indicative of one or more of the following: i) the degree of nicotine withdrawal they are experiencing, ii) the nicotine levels they are currently physiologically habituated to, and iii) their decreased dependence on nicotine. Such measurements can include one or more of blood pressure, heart rate, respiration and like measurements. For example, with decreased dependence, the patent's resting heart rate and blood pressure may be expected to decrease when they have not have a dose of nicotine within several hours compared to the time when they just started their smoking cessation program. Contrarily, after they have had a dose of nicotine, these parameters can be expected to increase relative to the time when just started their smoking cessation program. The measurements may be taking before during or after receiving a dose of nicotine compound either utilizing patch 15$cp$ and/or, electronic cigarette or an actual cigarette. Using the physiologic measurements, the reduction in nicotine delivered can be titrated to the patient's physiological response to their smoking cessation program including their decreased dependence on nicotine and in this way, facilitate a faster more successful program. With either approach, a dose delivery parameter, such as dose of nicotine delivered during a delivery period, can be stepped down in set increments of for example 1, 5, 10%, etc. which are determined based on one or more of the progress factors and/or physiological measurements. In yet another approach, a dose delivery parameter such as dose of nicotine delivered during a delivery period, can be decreased in such increments based on time since the patient started their smoking cessation program. For example, the dose of nicotine delivered during a delivery period, can be stepped down between about 1 to 10% each week from start of their smoking cessation program, as an alternative between about 5% to 20% every two week or even every month. What the approach, the decrease can be adjusted so that so that patient does not experience any significant feelings of withdrawal and/or nicotine cravings, thus improving patient compliance with the program and reducing the likelihood of relapse.

Embodiments for Treatment of Other Psychoactive Conditions

Due to the psychoactive effects of nicotine, in various embodiments, the methods and apparatus described herein may also be adapted for treatment of psychoactive and/or neurological conditions such as schizophrenia, ADHD, headache, migraine headache. In such embodiments, one or more of the "delivery parameters" defined herein such as the dose delivered during a delivery period, rate of delivery (e.g., flux of drug through the skin) and duration of delivery period and non-delivery period can be adjusted for treatment of the particular psychoactive condition. For example, for ADHD, longer duration periods can be used to provide the patient a steady delivery of therapeutic agent over an extended period, for example during a 12 hour period starting in the morning during the time that the patient is in school and after school doing homework. In such applications the delivery period waveform can include a rapid rise at the beginning of the delivery period (e.g., in the morning) to get the patient plasma concentration

EXAMPLES

Various embodiments of the invention are further illustrated with reference to the appended example which details the use of embodiments of a biphasic transdermal iontophoretic delivery system. Portions of the example are also described in a paper entitled: Biphasic Transdermal Iontophoretic Drug Delivery Platform (McLaughlin, G. W, et al Conf. Proc. IEEE Eng. Med. Biol. Soc. 2011 August; 2011:1225-8) which is incorporated by reference herein for all purposes. It should be appreciated that this example is presented for purposes of illustration and the invention is not to be limited to the information or the details therein. For example, while the example presented describes the delivery of ferrous chloride, it should be understood that various embodiments of the invention can be used for the delivery of any number of compounds using this approach including, for example, various nicotine compounds such one or more nicotine salts, opioid such as methadone, antiemetics, (e.g., Dimenhydrinate) and other therapeutic agents.

Methodology

System Description: One embodiment of a system that was tested for delivery of therapeutic agent comprised an active electrode, passive electrode, iontophoresis system and a programmer which are described below.

Active electrode: This was constructed by using a DuPel Model #198809-001 (Empi, Inc., Clear Lake, S. Dak., USA) electrode with the buffering agent removed and replaced with a teabag filled with two sheets of 3M gauze with 4.0 ml of solution. The solution was prepared by dissolving 1.2 g of $FeCl2$ (Sigma-Aldrich, St. Louis, Mo., USA) and 300 mg of Poly-Ethylene Oxide (PEO, Mol wt. 100 k) into 4 ml of DI water. The active electrode area was 13.3 cm2.

Passive electrode: This was constructed using a DuPel Model #198809-001 electrode with the buffering agent removed and replaced with a teabag filled with two sheets of 3M gauze and 300 mg of Polyethylene Oxide (PEO) with 4 ml of DI water added. The active electrode area was 13.3 cm2.

Iontophoresis system: This comprised a custom made unit that was controlled by a MSP430F428 (Texas Instruments, Dallas, Tex., USA) microcontroller. This microcontroller coordinated the activities between the switch states of an H-bridge circuit in conjunction with a variable current source. The H-bridge had a programmable voltage rail with a resolution of ~650 mV steps and a maximum compliance voltage of 80V. The variable current source had a programmable current target with a resolution of ~40 µxA with an upper limit of 5 mA. The microcontroller was able to update these values at a rate of 5 Hz along with measure and store their values with a time stamp for data archival purposes. Two AA batteries were used to power the system. These batteries were capable of providing up to 40 hours of operation under a standard therapy profile. FIG. 1 shows a picture of the system along with a simplified block diagram of the internals.

Programmer: This comprised a personal computer that was able to be interfaced to the iontophoresis system via a USB cable. The application code used to program the device was written in TCL/TK. This program was able to set the therapy pulse duration and current value along with the inhibit pulse duration and current value. It was also capable of specifying the total therapy duration. In addition, the programmer was also able to retrieve the data stored in the unit for analysis.

Experimental Setup: Ten in-vitro test chambers were constructed out of a block PTFE and filled with 120 ml of Hanks Buffered Salt Solution (HBSS). Freshly excised abdominal skin from a male Yorkshire pig (35 kg) was sectioned into 10 (100 mm×175 mm) pieces. Yorkshire pig skin was used as it has been shown to closely mimic the properties of human skin. The subcutaneous fat beneath the dermis layer of the skin was removed so that only the stratum corneum, epidermis, basal layer and dermis layers remained. The skin was then shaved and inspected for blemishes or scratches that might alter transport. Each test chamber had a piece of skin placed on top. Particular care was taken to not damage the integrity of the skin. The skin was affixed to the test chamber via 1¼" clips. The active and passive electrodes were then placed on the pig skin and attached to the iontophoresis system. All skin irregularities were avoided during this process.

The iontophoresis system was configured to provide a 6 hour therapy session. The first hour of the therapy session consisted of the system in an inhibit mode with a current value of −3 mA. The second hour of the therapy session was a drive mode with a current value of 3 mA. In hour 3 and 4 the system was in the inhibit mode with a current value of −3 mA. In hour 5 the system was in a drive mode with a current value of 3 mA and in hour 6 the system was in an inhibit mode with a current value of −3 mA.

The experimental chambers were placed on magnetic stirrer-hotplates to maintain the HBSS solution between 29° C. to 34° C., which kept the surface of the pig skin between 28° C. to 33° C. Samples of 1 ml were drawn every 15 minutes from the reservoir, using a 25 gauge needle. An equivalent volume of HBBS solution was replenished to maintain the level in the test chamber. During the data analysis, appropriate correction factors were used to compensate for this fluid replacement.

Upon completion of the therapy, the skin samples were visually examined for irritation and or staining. The samples were then photographed. The concentration of iron was quantified, after the required dilutions, by using a standard colorimetric assay. The samples were added to an acidic buffered reagent containing hydroxylamine, thiourea and Ferene (5,5' (3-(2-pyridyl)-1,2,4-triazine-5,6 diyl)-bis-2-furansulfonic acid, disodium salt). The acidic pH of the buffered reagent was used to release the ferric iron, which is then reduced to ferrous form by the hydroxylamine. This ferrous iron then reacted with the Ferene producing a colored complex. The absorption of this ferrous-Ferene complex was then read at 595 nm using a spectrophotometer (Multiscan EX; Thermo Electron Corporation, Vantaa, Finland). The absorption spectrum provided a proportional relationship to that of the iron concentration within the sample. This assay method provides a lower limit of quantification of 50 µg/dl.

Results

Figure 9:
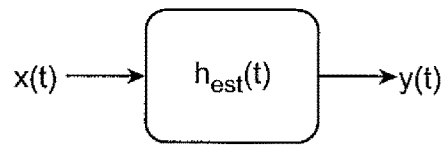
FIG. 9 is a block diagram of a transfer function used to model an embodiment of the transdermal iontophoretic delivery system used in the example.

The average of the ten samples was taken for each 15 minute sample period to obtain a mean cumulative density data set. This data set was then used as the measured output of the system to be identified, y(t). The input to the system was the known integral of the active portion of the therapy session, x(t). These sets of data were than used to identify the system transfer function, $h_{est}(t)$ which is shown in block diagram form in FIG. 9.

The transfer function $h_{est}(t)$ of the system was estimated based on Fourier transforms of the input and output signals on the system.

$$H(\omega) = \frac{\overline{X(\omega)} \cdot Y(\omega)}{|X(\omega)|^2} = \frac{\hat{R}_{xy}}{\hat{R}_{xx}}$$

An inverse Fourier transform was then taken of the resulting transfer function. This data set was then cropped, limiting the memory of the system transfer function to a period of 10 samples or 2.5 hours. The known input data was then convolved with this transfer function to obtain the estimated cumulative system density response. This data was then analyzed to determine how well the predicted output matched the measured output. This resulted in an R2 value of 0.912, confirming a good correlation between the model and the data.

Figure 10A:
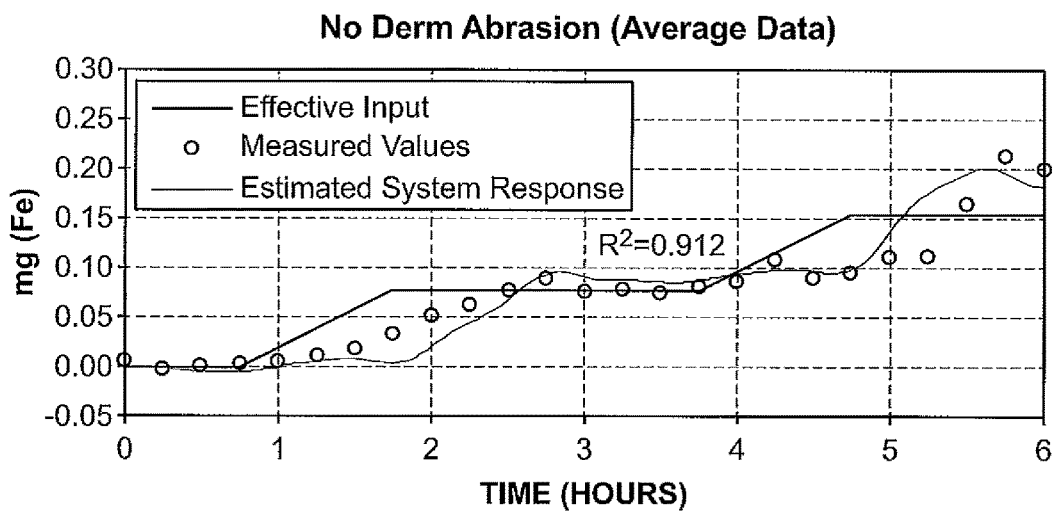
FIGS. 10a and 10b are plots of delivered therapeutic agent versus time.
Figure 10B:
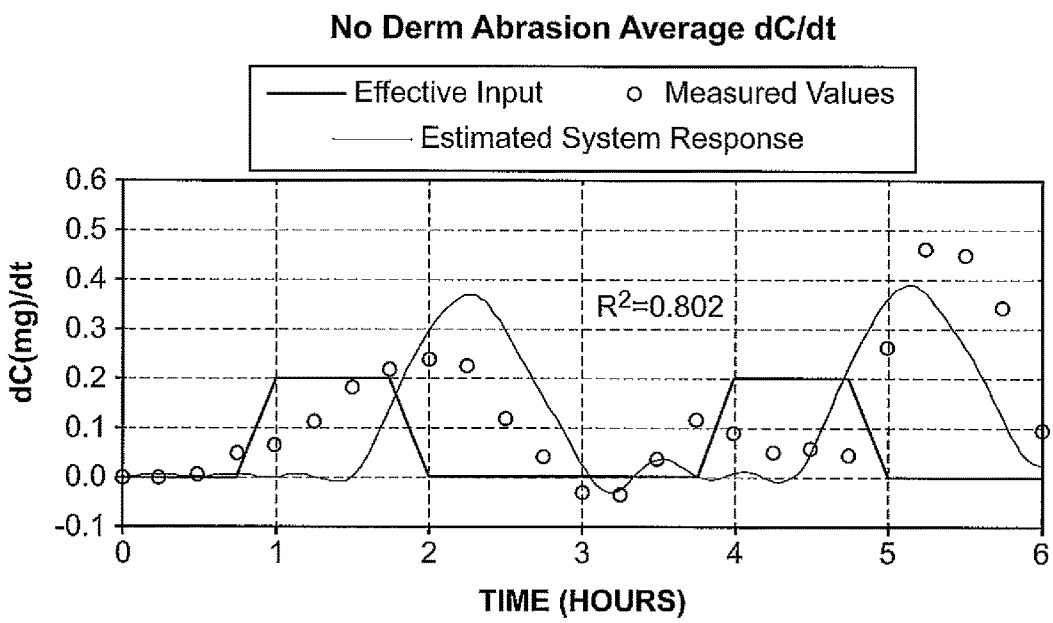

Next, the derivative of the measured cumulative density data was taken. In order to obtain an accurate estimate of the derivative of the data a first order least means squares fit was performed for each 4 samples of the data moving in a single sample step. The slope of this fit was then used as the representative value for the derivative of the data. This data was then analyzed using the same method as that of the cumulative density function data. This resulted in an $R^2$ value of 0.802, confirming that the predicted model correlated well with the estimated pulsatile drug delivery model as shown in FIGS. 10a and 10b.

The measured results show a time lag of around 45 minutes between the start of the therapy cycle and the detection of the $FeCl_2$ in the saline solution. This time lag is expected in the in-vitro studies due to the transport time required to traverse all the layers of the skin and reach the saline bath. In an in-vivo study this lag would be expected to be substantially smaller due to an active micro-capillary system just under the basal layer, alleviating the need for the material to pass through the dermis layer.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, the iontophoretic patch can be modified in size, shape and dose of therapeutic agent for different medical conditions, different tissue sites as well as for various pediatric applications. Additionally, the patch assemblies, methods and control algorithms can also be modified for skin type, therapeutic agent dose, as well as various pediatric applications.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. A system for transdermal iontophoretic delivery of a therapeutic agent to reduce an addictive craving in a patient, the system comprising an electrode assembly and a controller, the system configured to:
   position at least one electrode assembly in electrical communication with a skin of the patient, the at least one electrode assembly including a skin contacting layer and a solution comprising the therapeutic agent, wherein the therapeutic agent passively diffuses into the skin of the patient without application of an external force;
   deliver a dose of the therapeutic agent from the at least one electrode assembly into the skin of the patient during a first period using a first current having a polarity and magnitude to repel the therapeutic agent out of the electrode assembly, wherein delivering a dose of therapeutic agent includes a therapeutic agent delivery profile during the first period configured to mimic a delivery profile from the addictive craving;
   retain the therapeutic agent in the at least one electrode assembly during a second period using a second current having a polarity and magnitude to retain the therapeutic agent in the electrode assembly such that delivery of the therapeutic agent into the skin during the second period is minimized, wherein the first period comprises a delivery period and the second period comprises a non-delivery period, which together comprise a delivery cycle; and
   control the delivery cycle, wherein controlling the delivery cycle includes utilizing the controller to deliver or retain the therapeutic agent based on the delivery profile.

2. The system of claim 1, wherein the therapeutic agent comprises a nicotine compound for treatment of cravings and withdrawal from nicotine dependent addictions.

3. The system of claim 2, wherein the therapeutic agent comprises nicotine, a nicotine salt or a nicotine analogue.

4. The system of claim 1, wherein the therapeutic agent comprises a compound for treatment of cravings and withdrawal from opioid dependent addictions.

5. The system of claim 4, wherein the therapeutic agent comprises a methadone compound.

6. The system of claim 5, wherein the methadone compound comprises methadone, a methadone analogue or a methadone derivative.

7. The system of claim 1, wherein the therapeutic agent comprises a compound for treatment of cravings and withdrawal from cocaine addiction.

8. The system of claim 7, wherein the therapeutic agent comprises acetylcysteine, baclofen, bupropion, vanoxerine, or vigabatrin.

9. The system of claim 1, wherein the electrode assembly comprises a first electrode and a therapeutic agent reservoir electrically coupled to the first electrode and fluidically coupled to the skin contacting layer.

10. The system of claim 9, wherein the electrode assembly further comprises a second electrode.

11. The system of claim 1, wherein the delivery period is initiated by a patient input device, the patient input device generating a signal which is fed into the controller.

12. The system of claim 11, wherein the controller includes a control program or other logic for initiating a drug delivery period upon receiving the signal.

13. The system of claim 12, wherein the controller maintains the first current for the drug delivery period to deliver a selected dose of the therapeutic agent based on the delivery profile.

14. The system of claim 13, wherein the controller stops the first current and starts the second current by generating a holding current.

15. The system of claim 14, wherein the controller adjusts a magnitude of the first current or a magnitude of the second current relative to a concentration of the therapeutic agent within the solution.

16. The system of claim 1, wherein the delivery profile comprises a profile of an actual use of a chemical compound by the patient that results in the addictive craving of the patient.

17. The system of claim 1, wherein the controller is configured to limit a number of doses of therapeutic agent delivered over a selected period.

18. The system of claim 17, wherein the selected period is 24 hours.

19. The system of claim 17, wherein the therapeutic agent comprises a compound for treatment of nicotine cravings.

20. The system of claim 17, wherein the therapeutic agent comprises a compound for treatment of opioid cravings.

21. The system of claim 17, wherein the therapeutic agent comprises a compound for treatment of cocaine cravings.

22. The system of claim 1, wherein the controller is configured to limit a time interval between delivered doses of the therapeutic agent.

* * * * *